United States Patent [19]

de Castiglione et al.

[11] 4,350,627
[45] Sep. 21, 1982

[54] BIOLOGICALLY ACTIVE PEPTIDES

[75] Inventors: Roberto de Castiglione; Fiorenzo Faoro; Giuseppe Perseo; Silvano Piani; Francesco Santangelo, all of Milan, Italy

[73] Assignee: Farmitalia Carlo Erba S.p.A., Italy

[21] Appl. No.: 212,586

[22] Filed: Dec. 3, 1980

Related U.S. Application Data

[63] Continuation-in-part of Ser. No. 120,832, Feb. 12, 1980, abandoned.

[30] Foreign Application Priority Data

Sep. 20, 1979 [GB] United Kingdom ............... 7932590
Sep. 15, 1980 [GB] United Kingdom ............... 8015412

[51] Int. Cl.$^3$ .................... C07C 103/52; A61K 37/00
[52] U.S. Cl. .......................... 260/112.5 E; 424/177; 260/112.5 R
[58] Field of Search ............... 260/112.5 E, 112.5 R; 424/177

[56] References Cited

U.S. PATENT DOCUMENTS 4,254,024  3/1981  Stewart et al. ............... 260/112.5 E

OTHER PUBLICATIONS

Chem. Abstr. vol. 90, 1979 39277d.
Chem. Abstr. vol. 89, 1978 24818m.
Chem. Abstr. vol. 92, 1980 6947k.
Chem. Abstr. vol. 91, 1979 74908c.
Chem. Abstr. vol. 89, 1978 24818m.

Primary Examiner—Delbert R. Phillips
Attorney, Agent, or Firm—Stevens, Davis, Miller & Mosher

[57] ABSTRACT

There is disclosed biologically active peptides of the formula $$X-Tyr-A-Phe-B-C-W \quad (I)$$
$$\overset{|}{\underset{}{Y}}$$

where X is a hydrogen atom, an N-terminus protecting group (any of an acyl-type protecting group, an aromatic urethane-type protecting group, an alkyl-type protecting group, or an alkyl urethane type protecting group), or a residue of a natural L-amino acid or a dipeptide formed of two natural L-amino acids, wherein the free amino group may be replaced by any of the foregoing N-terminus protecting groups;

Y is a hydrogen atom or a protecting group for the phenolic hydroxyl group of tyrosine;

A is a D-amino acid residue with a lower (thio) alkyl side chain;

B is a neutral L-amino acid residue, a glycine residue, or an N-methyl amino acid residue;

C is a direct bond or an amino acid or di-or tripeptide residue; and

W is OH, OR, $NH_2$, NHR, $N(R)_2$, $NH-NH_2$, where R is an alkyl, cycloalkyl or aralkyl group of 1 to 7 carbon atoms or NHNHR' where R' is a hydrogen atom, linear or branched alkyl, cycloalkyl; alkenyl, a linear or branched or cyclic aliphatic urethane-type group, an aromatic urethane-type group normally used in polypeptide chemistry, a residue of an α-amino; α-imino, or β-amino acid, or a di-or tripeptide residue, where the -NHR' bond is an amidic linkage and the amino group is free or protected by an N-terminus protecting group. The peptides have central nervous system activity and are useful as analgesics, psychotics, and neuroendocrinologicals.

131 Claims, No Drawings

BIOLOGICALLY ACTIVE PEPTIDES

CROSS REFERENCE TO RELATED APPLICATIONS

This application is a continuation-in-part of copending application Ser. No. 120,832 filed Feb. 12, 1980, now abandoned.

GENERAL DESCRIPTION OF THE INVENTION

The present invention relates to new biologically active peptides, their pharmaceutically acceptable salts, processes for their preparation, and their application as therapeutic agents.

The invention relates more particularly to peptides of the general formula:

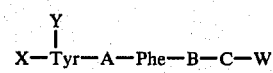

$$X—Tyr—A—Phe—B—C—W \quad (I)$$

wherein:

X is a hydrogen atom, an N-terminus protecting group selected from the group consisting of acyl-type protecting groups, aromatic urethane-type protecting groups, alkyl-type protecting groups, alipha tic urethane-type protecting groups, or, alternatively, a residue of a natural L-amino acid or a dipeptide from two natural L-amino acids, in which the free amino group may be replaced by any of the N-terminus protecting groups cited above;

Y is a hydrogen atom, or a protecting group for the phenolic hydroxyl group of tyrosine selected from the group consisting of tetrahydropyranyl, methyl, tert-butyl, trityl, benzyl, 2,4-dichlorobenzyl, benzyloxycarbonyl, 2-bromobenzyloxycarbonyl, tert-butyl oxycarbonyl, or lower acyl;

A is a D-amino acid residue with a side chain constituted by a lower alkyl or lower thioalkyl group;

B is a neutral L-amino acid residue, a glycine residue, or an N-methyl amino acid residue, such as sarcosine and L-N-methylphenylalanine;

C is a direct bond or a residue of an amino acid or a residue of a di- or tripeptide, and may be of α-amino, α-imino or β-amino acids, of either L or D configuration, provided they are not basic or acidic, and in the case of hydroxy amino acids such as tyrosine, serine, and threonine, the hydroxy group may be free or protected by one of the protecting groups referred above under Y; and W is OH, OR, $NH_2$, NHR, $N(R)_2$, $NH—NH_2$, where R is an alkyl, cycloalkyl, or aralkyl group having from 1 to 7 carbon atoms or NHNHR' wherein R' is a hydrogen atom, a $C_1$–$C_{10}$ linear or branched alkyl, cycloalkyl, including adamantyl, or aralkyl group; an alkenyl group having from 2 to 8 carbon atoms, a linear, branched, or cyclic aliphatic acyl-type group having from 1 to 16 carbon atoms, unsubstituted or substituted by hydroxy, amino, $C_1$–$C_4$ alkoxy or halogen atom, an aromatic acyl-type group, such as benzoic, phenylacetic, and cinnamic residue, unsubstituted or substituted by hydroxy, amino, halogen atom or $C_1$–$C_4$ alkoxy; a linear, branched, or cyclic $C_3$–$C_4$ alkoxy; a linear, branched, or cyclic $C_3$–$C_{11}$ aliphatic urethane-type group; an aromatic urethane-type group normally used in polypeptide chemistry, such as benzyloxy carbonyl; a residue of an α-amino acid, α-imino or β-amino acid, having either L or D configuration, or a residue of a di- or tripeptide, formed by α-amino, α-imino or β-amino acids, having either L or D configuration, where the bond

is an amidic linkage and the amino group of the residue may be free or protected by an N-terminus protecting group as defined supra.

Salts of the compounds of general formula (I) with trifluoroacetic acid, hydrofluoric acid, hydroboric acid, acetic acid, and hydrochloric acid as well as other pharmaceutically acceptable salts of compounds of general formula (I) are all within the scope of the present invention.

The synthesis of the peptides of the present invention may be accomplished by classical solution methods or by solid phase or polymeric supports. Examples of both procedures are given below. In the classical solution method, the synthesis consists essentially in appropriate successive condensations of protected amino acids or peptides. The condensation is carried out so that the resulting peptides have the desired sequence of 4–7 amino acid residues. The amino acids and peptides, which are condensed according to the method known per se in polypeptide chemistry, have their amino and carboxyl groups, which are not involved in the formation of the peptide linkage, blocked by a suitable protecting group.

The hydroxyl functions of hydroxylated amino acids may be protected by suitable protecting groups (throughout all the synthesis or only during a few steps) or they may be left unprotected. The protecting groups are capable of being removed by acidolysis, saponification, or hydrogenolysis. For the protection of the amino groups the following protective groups may for example be employed: benzyloxycarbonyl (Z), t-butyloxycarbonyl(Boc), tritylformyl, trifluoroacetyl and o-nitrophenylsulphenyl.

For the protection of the carboxyl groups the following protective groups may for example be employed: methyl, ethyl, tert-butyl, benzyl, and p-nitrobenzyl.

For the protection of the hydroxy groups the following protecting groups may for example be used: acetyl, tert-butyloxycarbonyl, benzyloxycarbonyl, 2-bromobenzyloxycarbonyl, tetrahydropyranyl, tert-butyl, trityl, benzyl, and 2,4-dichlorobenzyl.

The condensation between an amino group of one molecule and a carboxyl group of another molecule to form the peptidic linkage may be carried out through an activated acyl-derivative such as a mixed anhydride, an azide, an activated ester, and so on, or by direct condensation between a free amino group and a free carboxyl group, in the presence of a condensing agent such as dicyclo-hexyl-carbodimide, alone or together with a racemization preventing agent, such as N-hydroxysuccinimide or 1-hydroxybenzotriazole.

Hydrazido or substituted hydrazido derivatives in accordance with the present invention are prepared by (1) condensing the N-protected peptide or aminoacid with a suitably substituted hydrazine, such as benzylcarbazate, t-butylcarbazate, adamantyl-carbazate, phenylhydrazine, or adamantylhydrazine, or (2) reacting the N-protected peptide or aminoacid hydrazide with a suitable alkylating agent, such as an alkyl chloride, or with a suitable acylating agent such as benzylchloroformate, t-butylchloroformate, and adamantyl fluoroformate. The condensation may be carried out in a solvent such as dimethylformamide, pyridine, acetonitrile, tetrahydrofuran, and so on.

The reaction temperature may range between −30° C. and room temperature. The reaction time is generally from 1 to 120 hours.

The scheme of synthesis, the protecting groups, and the condensing agents are all selected so to avoid the risk of racemization. De-protecting reactions are carried out according to the methods known per se in polypeptide chemistry.

In the solid-phase method a polymeric support is used. The polymer is preferably a copolymer of styrene with 1–2 weight percent of divinylbenzene as a cross-linking agent which causes the polystyrene polymer to be completely insoluble in most organic solvents.

The synthesis is commenced from the C-terminal end of the peptide, by attaching the required amino acid to a chloro-methylated resin, a hydroxymethyl resin, or a benzhydrylamine resin.

The amino and side-chain protecting groups are those described in the classical solution synthesis.

In the preparation of the compounds of this invention, an amino-protected amino acid is coupled to the chloromethylated resin with the aid of, for example, cesium bicarbonate catalyst, or to a hydroxymethyl or benzhydrylamine resin with the aid of a condensing agent such as dicyclohexylcarbodiimide.

After the initial coupling, the amino-protecting group is removed by a choice of reagents including trifluoroacetic acid or hydrochloric acid solutions in organic solvents at room temperature. After removal of the amino-protecting group, the remaining protected amino acids are coupled stepwise in the desired order to obtain the desired peptide.

Each protected amino acid is generally reacted in a 3-fold excess using an appropriate carboxyl group activator such as dicyclohexylcarbodiimide in solution, for example, methylene chloride-dimethylformamide mixtures.

After the desired amino acid sequence has been completed, the desired peptide is removed from the resin support by treatment with a reagent such as hydrogen fluoride, which not only cleaves the peptides from the resin, but also cleaves most of the remaining side-chain protecting groups. When a chloromethylated or hydroxymethylated resin is used, the hydrogen fluoride treatment results in the formation of the free peptide acid (W=OH). When a benzhydrylamine resin is used, the hydrogen fluoride treatment results directly in the free peptide amide (W=NH$_2$). Alternatively, when the chloromethylated or hydroxymethylated resin is employed, the side-chain protected peptide can be cleaved by treatment of the peptide resin with ammonia or an alkyl or dialkylamine to give the desired side-chain protected amide, alkylamide or dialkylamide (W=NH$_2$, NHR, NR$_2$). The side-chain protection may then be removed by any of the methods known in the art.

In preparing the esters of the present invention (W=OR), the resins used to prepare the acid (W=OH) are employed and the side-chain protected peptide is cleaved with a base and the appropriate alcohol. The side-chain protection is then removed in the usual way.

Alternatively, the peptide acids and amides can be obtained from the peptide esters by saponification or ammonolysis.

DETAILED DESCRIPTION OF THE INVENTION

When X is an acyl-type protecting group, it is conveniently formyl, acetyl, trifluoroacetyl, propionyl, or benzoyl; when X is an aromatic urethane-type protecting group, it is conveniently benzyloxycarbonyl; 2,4-dichlorobenzyloxy-carbonyl, 2-bromobenzyloxycarbonyl, 4-nitro-benzyloxycarbonyl; or 4-methoxybenzyloxycarbonyl; when X is an aliphatic urethane-type protecting group, it is conveniently tert-butyloxycarbonyl, 1-methylcyclobutyloxycarbonyl, adamantyloxycarbonyl and isobornyloxycarbonyl; when X is an alkyl-type protecting group, it is conveniently trityl, benzyl, methyl, ethyl, or isopropyl; when X is a natural L-amino acid residue, it is preferably selected from the group consisting of Gly, Ala, Leu, Met, Lys, Arg, His, Phe, Trp, Ser, and Thr; when X is a dipeptide from two natural L-amino acids, it is preferably from two L-amino acids selected from the group cited hereinabove and conveniently it is Arg-Arg, Arg-Lys, Lys-Arg, Lys-Lys, Leu-His, His-Leu, Leu-Leu, Leu-Met, Met-Leu, Leu-Trp, Trp-Leu, Thr-Ala, Ala-Thr, Ser-Ala, and Ala-Ser.

A is preferably a D-amino acid residue selected from the group consisting of ala, val, ile, leu, pro, ser, thr, met, met-sulphoxide, and S-ethyl-homocysteine. The small letters indicate D-amino acid residues.

B is a neutral L-amino acid residue conveniently selected from the group consisting of α-aminophenylacetic acid (Phg), Ala, Val, Ile, Leu, Pro, Met, Ser, Thr, Phe, Tyr, Trp, a glycine residue or an N-methylaminoacid residue, such as sarcosine, L-N-methylalanine, and L-N-methyl-phenylalanine.

C may be direct bond or a residue of an amino acid or a residue of a di- or tripeptide, and may be of (1) an α-amino acid residue, conveniently selected from the group consisting of Gly, Ala, Val, normal valine (Nva), Leu, Ile, α-amino-n-butyric acid (Abu), Phg, Phe, Trp, Tyr, Ser, Thr, Homoserine (Hse), Met, Met-sulfoxide, β-cyclohexylalanine, and para-substituted Phe, the substituent being selected from the group consisting of chlorine, bromine, fluorine, amino and nitro; (2) an α-imino acid, conveniently selected from the group consisting of Pro, 3-hydroxyproline, 4-hydroxyproline, pipecolic acid, 2-azetidinecarboxylic acid, 4-thiazolidine carboxylic acid, Δ$^3$-proline; (3) a β-amino acid, conveniently selected from the group consisting of β-alanine, β-phenyl-β-aminopropionic acid, β-aminobutyric acid; (4) an N-methyl amino acid residue, conveniently selected from the group consisting of Sar, N-methyl-phenylalanine (MePhe), N-methylalanine (MeAla); all of either L or D configuration, provided they are not basic or acidic; of (5) a dipeptide which may be conveniently selected from dipeptides resulting from the condensation of α-amino, β-amino, α-imino and N-methyl amino acids which are as hereinabove defined, provided that the two amino acids are not the same; of (6) a tripeptide residue which may be conveniently selected from tripeptides J-L-M wherein (a) J is Tyr, Trp, Phe, Phg, hexahydro-Phe, Gly, Val and para-substituted Phe, the substituent being selected from the group consisting of chlorine, bromine, fluorine, amino, and nitro, (b) L is Val, Leu, Ile, Gly, Ala, Nva, Sar, MePhe, MeAla, and β-amino or α-imino acids which are hereinabove defined, and (c) M is Ser, Hse, Thr, Abu, or Gly provided that J is different from L and L is different from M.

Hydroxyamino acids are unprotected or protected by a protecting group for the hydroxy function. Suitable protecting groups are methyl, tert-butyl, trityl, benzyl, 2,4-dichlorobenzyl, benzyloxycarbonyl, 2-bromobenzyloxycarbonyl, tert-butyloxycarbonyl, or lower acyl, conveniently formyl, acetyl, trifluoroacetyl, propionyl, and benzoyl.

W is OH, OR, $NH_2$ NHR, $N(R)_2$, or NHNHR', wherein R is a $C_1$-$C_{10}$ linear or branched alkyl, conveniently methyl, ethyl, n-propyl, isopropyl, n-butyl, sec-butyl, iso-butyl, and 2,2,2 trifluoro ethyl, $C_1$-$C_{10}$ cycloalkyl, conveniently cyclohexyl or adamantyl, or $C_6$-$C_8$ aralkyl, conveniently phenyl, benzyl or phenylethyl; and R' is a hydrogen atom, a $C_2$-$C_{10}$ linear or branched alkyl, cycloalkyl or $C_6$-$C_8$ aralkyl, conveniently as hereinabove defined under R, an alkenyl group having from 2 to 8 carbon atoms, preferable allyl; a linear, branched, or cyclic aliphatic acyl-type group having from 1 to 16 carbon atoms, conveniently formyl, acetyl, propionyl, butyryl, lauryl, and 1-adamantancarbonyl, unsubstituted or substituted by hydroxy, amino, $C_1$-$C_4$ alkoxy, or halogen atom, (a valuable example of this substituted aliphatic acyl-type group is trifluoroacetyl), an aromatic acyl-type group, such as benzoyl, phenylacetyl, and cinnamyl residue, unsubstituted or substituted by hydroxy, amino, halogen atom or $C_1$-$C_4$ alkoxy; a linear, branched or cyclic $C_3$-$C_{11}$ aliphatic urethane-type group, conveniently as defined under X, and an aromatic urethane-type group conveniently as defined under X.

When Y is lower acyl, it is conveniently formyl, acetyl, trifluoroacetyl, propionyl, or benzoyl.

The Rf values are determined on precoated plates of silica gel 60 $F_{254}$ (Merck), layer thickness 0.25 mm, length of the plate 20 cm, using the following development systems:

System A: benzene-ethyl acetate-acetic acid-water (10:10:2:1) (upper phase)

System B: benzene-ethyl acetate-acetic acid-water (100:100:40:15) (upper phase)

System C: n-butyl alcohol-acetic acid-water (4:1:1)

System D: chloroform-methyl alcohol—32% ammonium hydroxide (65:45:20)

Symbols herein are those commonly used in peptide chemistry. In the following examples D-amino acid residues are designated by small letters, e.g., ala=D-Ala; Adoc represents adamatyloxycarbonyl, and Ad represents adamantyl.

TLC analyses are carried out under no standard conditions, the Rf values can therefore change, particularly at different temperatures. Melting points are determined in open capillaries and are uncorrected. Most of the derivatives soften and decompose (dec.) before melting. Solvents for crystallization, precipitation, or grinding are reported in brackets.

High voltage paper electrophoresis is carried out with a Pherograph-Original-Frankfurt Type 64 apparatus on Schleicher and Schull paper No. 2317 at pH 1.2 (formic acid-acetic acid-water 123:100:777) at 1600 V (40 V/cm) and at pH 5.8 (pyridine-acetic acid-water 450:50:4500) at 1400 V (32.5 V/cm). Electrophoretic mobilities (E 1.2 and E 5.8) are given relative to that of glutamic acid.

The compounds of general formula (I) show interesting pharmacological activities in tests carried out on laboratory animals. More particularly, the compounds of general formula (I) show activity on the central nervous system as analgesics, antipsycotics, and neuroendocrinologicals.

Analgesic activity has been assessed in mice by the tailpinch test, as described by HAFFNER in Deutsch.Med.Worschr., 55:731, 1929. The tested substances were administered by i.v., s.c., i.p., or oral route. When administered by i.v. or s.c., the tested products displayed an analgesic effect at doses generally from 0.2 to 50 mg/kg.

The compounds of general formula (I) show receptorial affinities to central analgesic drugs when tested "in vitro" on rat brain according to the procedure described by PERT and SNYDER in Molec.Pharmacol., 10, 878, 1974. According to these properties the compounds of general formula (I) may find a therapeutic application for treatment of pains.

The compounds of general formula (I) also display activity on the central nervous system with the characteristic properties of antipsychotic drugs, as shown by tests carried out on rats according to the procedure described by JANSSEN, JAGENEAU, and SCHELLEKENS in Psychopharmacologia (Berl,), 1, 389, 1960. Active doses are generally from 0.2 to 60 mg/kg. According to this activity, the compounds of general formula (I) may find a therapeutic application as antipsychotic drugs.

The compounds of general formula (I) stimulate, among others, the release of growth-hormone and of prolactin as shown by ratio-immuno assays in the rat which were carried out according to the procedure described by NISWENDER, CHEN, MIDGLEY, METTES, and ELLIS, Proc.Soc.Exp.Biol.Med., 130, 793, 1968. Active doses are generally from 0.01 to 10 mg/kg. According to this activity, the compounds of general formula (I) may find a therapeutic application for stimulating the release of growth-hormone and prolactin.

Accordingly, therapeutic applications of the compounds of general formula (I) are also within the scope of the present invention. For therapeutic purposes, the compounds of general formula (I) and their salts are administered together with conventional pharmaceutically acceptable carriers or diluents.

The following examples are illustrative of the compounds of the present invention and are not limitative.

EXAMPLE 1

Preparation of
H-Tyr-ala-Phe-Gly-Tyr-Pro-Ser-$NH_2$.$CF_3COOH$ (13)

Step 1. Boc-Pro-Ser-$NH_2$ (1)

To a solution of 1.00 g (4.65 mmoles) Boc-Pro-OH in 10 ml anhydrous tetrahydrofuran, 0.52 ml (4.65 mmoles) N-methylmorpholine, and 0.45 ml (4.65 mmoles) ethyl chloroformate are successively added at a temperature of $-12°$ C. After stirring at this temperature for 2 minutes, a cold solution of 0.48 g (4.65 mmoles) H-Ser-$NH_2$ (R. W. Hanson and H. N. Rydon, J. Chem. Soc., 836, 1964) in 10 ml dimethylformamide is added. The reaction mixture is stirred at $-10°$ C. for 3 hours and at 20° C. for 1 hour, then filtered from salts and evaporated in vacuo. The residue is taken up with tetrahydrofuran, filtered, and the solution evaporated again in vacuo. By crystallization from methanol-diethylether 1.1 g of compound (1) are obtained: m.p. 138° C. $[\alpha]_D^{25}$ $-58.9°$ (c=1, MeOH); $Rf_A=0.15$; $Rf_B=0.33$.

Step 2. H-Pro-Ser-NH$_2$.CF$_3$COOH (2)

1.0 g. (3.3 mmoles) Boc-Pro-Ser-NH$_2$ (1) is dissolved in 10 ml trifluoroacetic acid at 0° C. After 30 minutes at 0° C. the solution is evaporated in vacuo, diluted with methanol, and evaporated again in vacuo. The product (2) is isolated from diethylether-petroleum ether: 1.0 g, m.p. 48°–50° C.; Rf$_C$=0.10.

Step 3. Boc-Tyr (Bzl)-Pro-Ser-NH$_2$ (3)

A solution of 1.0 g (3.2 mmoles) H-Pro-Ser-NH$_2$.CF$_3$COOH (2) in 35 ml dimethylformamide is cooled at 0° C., then 0.36 ml (3.2 mmoles) N-methylmorpholine are added, followed by 1.2 g (3.2 mmoles) Boc-Tyr (Bzl)-OH, 0.43 g (3.2 mmoles) 1-hydroxybenzotriazole, and 0.73 g (3.52 mmoles) dicyclohexylcarbodiimide. The reaction mixture is stirred for 1 hour at 0° C. and at room temperature overnight, then it is filtered, and evaporated in vacuo. The residue is dissolved in ethyl acetate and the solution washed successively with NaCl-saturated solutions of 1 M citric acid, 1 M NaHCO$_3$, and water. The organic solution is dried over anhydrous Na$_2$SO$_4$ and the solvent removed in vacuo. The (3) product is recovered by crystallization from ethyl acetate-petroleum ether: 1.4 g, m.p. 115° C.; $[\alpha]_D^{25}$−22.9° (c=1, MeOH); Rf$_A$=0.20

Step 4. H-Tyr (Bzl)-Pro-Ser-NH$_2$.CF$_3$COOH (4)

Operating as in Step 2, from 1.0 g (1.8 mmoles) Boc-Tyr (Bzl)-Pro-Ser-NH$_2$ (3) 1.0 g of compound (4) are obtained; $[\alpha]_D^{25}$−7.4° (c=1, MeOH); Rf$_C$=0.59; m.p. 54°–57° C. (dec.)

Step 5. Boc-Phe-Gly-NH-NH-Z (5)

0.42 ml (3.8 mmoles) N-methylomorpholine and 0.3 ml (3.8 mmoles) ethylchloroformate are successively added at −12° C. to a solution of 1.0 g (3.8 mmoles) Boc-Phe-OH in 10 ml anhydrous tetrahydrofuran. After stirring at this temperature for 2 minutes, a cold solution of 0.95 g (3.7 mmoles) H-Gly-NH-NH-Z.HCl (K. Hoffmann et al, J. Amer, Chem, Soc. 94, 6171, 1972) and 0.4 ml (3.7 mmoles) N-methylmorpholine in 15 ml dimethylformamide is added. The reaction mixture is stirred at −10° C. for 3 hours and at 20° C. for 1 hour, then filtered from salts and evaporated in vacuo. The residue is dissolved in ethyl acetate and washed several times successively with NaCl-saturated solutions of 1 M citric acid, 1 M NaHCO$_3$, and water. The organic layer is dried over anhydrous Na$_2$SO$_4$ and the solvent removed in vacuo. The product (5) (1.4 g) is recovered from methanol-diisopropyl ether: m.p. 143° C.; $[\alpha]_D^{25}$+5.6° (c=1, MeOH); Rf$_A$=0.63.

Step 6. H-Phe-Gly-NH-NH-Z.HCl (6)

1.0 g (2.1 mmoles) Boc-Phe-Gly-NH-NH-Z (5) is treated for 30 minutes at room temperature with 10 ml of a 1.3 N solution of hydrogen chloride in glacial acetic acid. Removal of the solvent in vacuo at 30° C., and grinding of the residue with diethylether, gives 0.89 of (6), m.p. 178° C.; $[\alpha]_D^{25}$+45° (c=1, MeOH); Rf$_C$=0.78; E$_{1.2}$=0.88.

Step 7 Boc-ala-Phe-Gly-NH-NH-Z (7)

Starting from 1.0 g (5.3 mmoles) Boc-ala-OH and 2.09 g (5.1 mmoles) H-Phe-Gly-NH-NH-Z.HCl (6), and operating as in Step 5, compound (7) (2.5 g) is obtained from methanol-diisopropyl ether: m.p. 165° C.; $[\alpha]_D^{25}$+8° (c=1, MeOH); Rf$_A$=0.51.

Step 8. H-ala-Phe-Gly-NH-NH-Z.HCl (8)

Starting from 1.0 g (1.8 mmoles) Boc-ala-Phe-Gly-NH-NH-Z (7) and operating as in Step 6, 0.84 g of (8) are obtained: m.p. 180° C.; $[\alpha]_D^{25}$+0.2° (c=1, MeOH); Rf$_C$=0.75. E$_{1.2}$=0.80.

Step 9. Boc-Tyr-ala-Phe-Gly-NH-NH-Z (9)

Starting from 1.0 g (3.5 mmoles) Boc-Tyr-OH and 1.65 g (3.4 mmoles) H-ala-Phe-Gly-NH-NH-Z.HCl (8) and operating as in Step 5, 2.24 g of (9) are obtained (crystallization from methanol-diisopropyl ether); m.p. 148° C.; $[\alpha]_D^{25}$+16.2° (c=1, MeOH); Rf$_A$=0.38.

Step 10. Boc-Tyr-ala-Phe-Gly-NH-NH$_2$ (10)

1.0 g (1.4 mmoles) Boc-Tyr-ala-Phe-Gly-NH-NH-Z (9) in 10 ml methanol is hydrogenated at room temperature in the presence of 0.27 g 10% Pd/C. The catalyst is removed by filtration and the solution concentrated in vacuo. By dilution with ethyl acetate 0.64 g of compound (10) is obtained, m.p. 148° C.; $[\alpha]_D^{25}$+26.6° (c=1, MeOH); Rf$_B$=0.34. E$_{1.2}$=0.57.

Step 11. Boc-Tyr-ala-Phe-Gly-Tyr (Bzl)-Pro-Ser-NH$_2$ (11)

To a solution of 2.0 g (3.5 mmoles) Boc-Tyr-ala-Phe-Gly-NH-NH$_2$ (10) in 20 ml anhydrous dimethylformamide, 2.18 ml (8.75 mmoles) 4 N hydrogen chloride in anhydrous tetrahydrofuran and 0.45 ml (3.85 mmoles) n-butyl nitrite are successively added at a temperature of −30° C. After stirring at this temperature for 30 minutes, 1 ml (8.75 mmoles) N-methylmorpholine is added, followed by a cold solution (−30° C.) of 1.66 g (2.91 mmoles) H-Tyr (Bzl)-Pro-Ser-NH$_2$.CF$_3$COOH (4) and 0.33 ml (2.91 mmoles) N-methylmorpholine in 40 ml dimethylformamide. The reaction mixture is allowed to react at −9° C. for three days, then the salts are filtered off, the solvent is removed in vacuo, and the product is precipitated from methanol-ethyl acetate-diethyl ether. The crude product is purified by column chromatography on silica gel (Merck), 70-230 mesh, eluting with ethyl acetate-methanol (8:2), 2.0 g of (11) are obtained from methanol-diethyl ether; m.p. 135° C.; $[\alpha]_D^{25}$−5.3° (c=1, MeOH); Rf$_B$=0.24.

Step 12. Boc-Tyr-ala-Phe-Gly-Tyr-Pro-Ser-NH$_2$. (12)

1.3 g (1.3 mmoles) Boc-Tyr-ala-Phe-Gly-Tyr (Bzl)-Pro-Ser-NH$_2$ (11) dissolved in 20 ml methanol are hydrogenated at 35° C. in the presence of 0.30 g 10% Pd/C. The catalyst is removed by filtration, and the solution is concentrated in vacuo. By dilution with diethyl ether 1.1 g of compound (12) are obtained, m.p. 160°–163° C. (dec.), $[\alpha]_D^{25}$−7.6° (C=1, MeOH); Rf$_B$=0.11; Rf$_C$=0.80.

Step 13. H-Tyr-ala-Phe-Gly-Tyr-Pro-Ser-NH$_2$. CF$_3$COOH (13)

1.0 g (1.1 mmoles) Boc-Tyr-ala-Phe-Gly-Tyr-Pro-Ser-NH$_2$ (12) is treated for 30 minutes at 0° C. with 10 ml trifluoroacetic acid. The solvent is removed in vacuo and the residue is ground with diethyl ether, giving 0.90 g of (13), m.p. 159°–160° C. $[\alpha]_D^{25}$+5.5° (C=1, MeOH); Rf$_C$=0.51.

EXAMPLE 2

Preparation of H-Tyr-ala-Phe-Gly-Tyr-NH$_2$.CF$_3$COOH (15)

Step 1. Boc-Tyr-ala-Phe-Gly-Tyr-NH$_2$ (14)

2.74 g (4.8 mmoles) Boc-Tyr-ala-Phe-Gly-NH-NH$_2$ (10) are dissolved in 50 ml anhydrous dimethylformamide and cooled at −30° C. 2.0 ml (12 mmoles) 6 N hydrogen chloride in anhydrous tetrahydrofuran and 0.63 ml (5.28 mmoles) n-butyl nitrite are successively added and the reaction mixture is stirred for 30 min. at −30° C. 1.34 ml (12 mmoles) N-methyl-morpholine are added at −40° C., followed by a precooled (−40° C.) solution of 0.865 g (4.0 mmoles) H-Tyr-NH$_2$.HCl (K. Blau and S. G. Waley, Biochem. J., 57, 538, 1954) and 0.456 ml (4.0 mmoles) N-methylmorpholine in 50 ml dimethylformamide. The reaction mixture is allowed to react for 7 days at −10° C., then it is concentrated to small volume, filtered from salt, and the product precipitated by dilution with chloroform. By crystallization from methyl alcohol-chloroform, 2.0 g of (14) are obtained, m.p. 127°-129° C.; $[\alpha]_D^{25}+19.9°$ (C=1, MeOH); Rf$_A$=0.15, Rf$_B$=0.56.

Step 2. H-Tyr-ala-Phe-Gly-Tyr-NH$_2$.CF$_3$COOH (15)

1.0 g (1.4 mmoles) Boc-Tyr-ala-Phe-Gly-Tyr-NH$_2$ (14) is made to react with 12 ml trifluoroacetic acid for 30 min. at 0° C. The acid is evaporated in vacuo, and the residue ground with diethyl ether. By crystallization from isopropyl alcohol diisopropyl ether, 0.94 g of (15) are obtained, m.p. 145°-146° C.; $[\alpha]_D^{25}+34.5°$ (C=1 MeOH); Rf$_C$=0.65.

Solid-phase synthesis. The synthesis on a polymeric support can be carried out, for example, by one of the following procedures:

Procedure A. Preparation of Boc-(AA)$_n$-(AA)$_{n-1}$ . . . (AA) Hydroxymethyl Polystyrene Ester Chloromethylated polystyrene resin is esterified with the first Boc-amino acid (Boc-AA$_1$-OH) according to Gisin, Helv. Chim. Acta, 56, 1476 (1973). The polystyrene ester is treated according to Schedule A for the incorporation of Boc-(AA)$_2$-OH, —Boc-(AA)$_n$-OH to give the title resin.

Schedule A

1. Wash with CH$_2$Cl$_2$×3;
2. Treat with TFA-CH$_2$Cl$_2$ (1:1) twice for 1 min.;
3. Treat with TFA-CH$_2$Cl$_2$ (1:1) for 30 min.;
4. Wash with CH$_2$Cl$_2$×4;
5. Treat with 10% TEA in CH$_2$Cl$_2$ twice for 1 min.;
6. Treat with 10% TEA in CH$_2$Cl$_2$ for 10 min.;
7. Wash with CH$_2$Cl$_2$×3;
8. Wash with DMF×3;
9. Wash with CH$_2$Cl$_2$×3;
10. Add 2 or 3 equivalents of the symmetrical anhydride of the corresponding amino acid derivative, prepared as described by Hagenmayer and Frank, Hoppe-Seyler's Z.Physiol.Chem., 353, 1973 (1972), dissolved in CH$_2$Cl$_2$. Reaction time 1-2 hours.
11. Wash with CH$_2$Cl$_2$×3;
12. Wash with isopropyl alcohol×3;
13. Wash with CH$_2$Cl$_2$×3;
14. Test ninhydrin reaction according to Kaiser et al, Annal.Biochem., 34, 595 (1970). In case of incomplete reaction repeat procedures 4 to 14 as above.

The abbreviations for solvents or reagents employed in Schedule A are as follows:
TFA: Trifluoroacetic acid.
TEA: Triethylamine
DMF: Dimethylformamide.

Procedure B. Preparation of H-(AA)$_n$-(AA)$_{n-1}$ . . . (AA)$_1$-Hydroxymethyl Polystyrene Ester After introduction of the last amino acid derivative according to Schedule A (Procedure A), wash the resin 3 times with acetic acid, repeat procedures 1 to 9, and wash 4 times with isopropyl alcohol.

Procedure C. Preparation of Boc-(AA)$_n$-(AA)$_{n-1}$ . . . (AA)$_1$-Benzhydrylamine Resin Boc-(AA)$_1$-OH is attached to the benzhydrylamine resin via dicyclohexylcarbodiimide, as described by Pietta et al, J.Org.Chem., 39, 44 (1974). Unreacted amino groups are acetylated with acetic anhydride/pyridine/CH$_2$Cl$_2$ (2:1:10). The polystyrene amide is then treated according to Schedule A (Procedure A) for the incorporation of the other amino acid residues to give the title resin.

Procedure D. Preparation of H-(AA)$_n$-(AA)$_{n-1}$ . . . (AA)$_1$-Benzhydrylamine Resin Operate as in Procedure B starting from the peptide resin of Procedure C.

EXAMPLE 3

Preparation of H-Tyr-ala-Phe-Gly-OMe (16)

1 g peptide resin of Procedure B with the required sequence of amino acid residues (introduced as Boc-Gly-OH, Boc-Phe-OH, Boc-ala-OH and Boc-Tyr-OH, in that order) is suspended in 25 ml methyl alcohol and 2 ml triethylamine for 3 days at room temperature. The resin is filtered off, washed with dimethylformamide, and the solvent evaporated in vacuo. By crystallization of the residue from isopropyl alcohol, 0.16 g of the title compound (16) is obtained, m.p. 216°-218° C.; $[\alpha]_D^{28}-32.6°$ (C=1, DMF); Rf$_C$=0.70. Amino acid ratios: Gly 1.04; ala 1.06; Tyr 0.99; Phe 1.00.

EXAMPLE 4

Preparation of H-Tyr-ala-Phe-Gly-OH (17)

(i) 1 g of the same peptide resin as in Example 3 is treated for 45 min. at 0° C. with 10 ml anhydrous (distilled over CoF$_3$) HF containing 1 ml anisole. The hydrogen fluoride is evaporated under reduced pressure and the anisole is removed by washing with diisopropyl ether. The crude peptide is extracted from the resin with 50% acetic acid, then purified by chromatography on a column of Sephadex G-15 by elution with 0.5 N acetic acid, and finally transformed into the acetate by treatment with amberlite IRA-45 (CH$_3$COO−).

(ii) Alternatively, 0.10 g peptide ester (16) are suspended in 5 ml H$_2$O and 3 ml methyl alcohol and saponified with 0.32 ml 1 N NaOH for 90 min. at room temperature. 0.32 ml 1 N HCl are added, and the solution concentrated in vacuo. By dilution with 95% ethanol 0.08 g of the title compound (17) is obtained, m.p. 250°-252° C. (dec.); $[\alpha]_D^{28}-2.8°$ (C=1, DMF), Rf$_C$=0.56. Amino acid ratios: Gly 1.04; ala 0.94; Tyr 1.00; Phe 1.05.

EXAMPLE 5

Preparation of H-Tyr-ala-Phe-Gly-NH$_2$ (19)

(i) 1 g of the same peptide resin as in Example 3 is suspended in 10 ml of a (1:1) mixture of methyl alcohol-dimethylformamide, and saturated at 0° C. with ammonia. The reaction mixture is stirred for 3 days at room temperature, then the resin is filtered off, washed with dimethylformamide, and the solvents evaporated in vacuo. The residue is treated with a solution of hydrogen chloride in anhydrous tetrahydrofuran and the product recovered as hydrochloride from isopropyl alcohol. 0.09 g of the title compound (19) is obtained, m.p. 206° C.; $[\alpha]_D^{28} +49.9°$ (C=1, MeOH), Rf$_C$=0.58. Amino acid ratios: Gly 1.05; ala 1.00; Tyr 0.91; Phe 1.03.

(ii) Alternatively, the same peptide (19) may be obtained from the peptide resin of Procedure D (with the required sequence of amino acid residues), by operating in the same way as described in Example 4(i).

By the classical solution procedure the following other derivatives have also been synthesized:

(20) H-Tyr-ala-Phe-Gly-NH-NH$_2$.2 HCl m.p. 190°–195° C. (dec.) (diethyl ether); Rf$_C$ 0.50; E$_{1,2}$ 1.09.

(21) H-Tyr-ala-Phe-Sar-NH-NH$_2$.2 HCl m.p. 193°–197° C. (dec.) (tetrahydrofuran); Rf$_C$ 0.47; E$_{1,2}$ 1.12.

(22) H-Tyr-ala-Phe-Sar-NH-NH-Z.HCl m.p. 150°–155° C. (dec.) (ethyl acetate); Rf$_C$ 0.70; E$_{1,2}$ 0.59.

(23) Boc-Tyr-ala-Phe-Sar-NH-NH$_2$ m.p. 110°–115° C. (dec.) (ethyl acetate-diethyl ether); Rf$_B$ 0.32; E$_{1,2}$ 0.57.

(24) Boc-Tyr-ala-Phe-Phe-NH-NH$_2$ m.p. 180°–183° C. (dec.) (ethyl acetate); Rf$_B$ 0.54; E$_{1,2}$ 0.49.

(25) H-Tyr-ala-Phe-Gly-Tyr-Pro-NH$_2$.HCl m.p. ca. 200° C. (dec.) (ethyl acetate); Rf$_C$ 0.58; E$_{1,2}$ 0.59.

(26) H-Tyr-ala-Phe-Gly-Tyr-(Bzl)-Pro-NH$_2$.HCl m.p. ca. 180° C. (dec.) (diethyl ether); Rf$_C$ 0.63. E$_{1,2}$ 0.53.

(27) Boc-Tyr-ala-Phe-Gly-Tyr-Pro-NH$_2$ m.p. 170° C.–175° C. (dec.) (diisopropyl ether); Rf$_B$ 0.24.

(28) Boc-Tyr-ala-Phe-Gly-Tyr (Bzl)-Pro-NH$_2$ m.p. 143° C. (diethyl ether) Rf$_B$ 0.47.

(29) H-Tyr-ala-Phe-Gly-Tyr-Ser-NH$_2$.CF$_3$COOH m.p. 150°–153° C. (dec.) (diethyl ether); Rf$_C$ 0.59; E$_{1,2}$ 0.57.

(30) Boc-Tyr-ala-Phe-Gly-Tyr-Ser-NH$_2$ m.p. ca. 100° C. (dec.) (ethyl acetate); Rf$_B$ 0.15; Rf$_C$ 0.83.

(31) H-Tyr-ala-Phe-Gly-Tyr-Hyp-Ser-NH$_2$.HCl m.p. 210°–220° C. (dec.) (isopropyl alcohol-diethyl ether); Rf$_C$ 0.44; Rf$_D$ 0.66; E$_{1,2}$ 0.51.

(32) H-Tyr-ala-Phe-Gly-Tyr-(Bzl)-Hyp-Ser(Bzl)-NH$_2$.HCl m.p. 175°–180° C. (dec.) (methyl alcohol-diethyl ether) Rf$_C$ 0.67; E$_{1,2}$ 0.44.

(33) Boc-Tyr-ala-Phe-Gly-Tyr-Hyp-Ser-NH$_2$ m.p. 156°–160° C. (dec.) (ethyl acetate-diethyl ether); Rf$_C$ 0.75.

(34) Boc-Tyr-ala-Phe-Gly-Tyr (Bzl)-Hyp-Ser (Bzl)-NH$_2$ m.p. 130°–136° C. (dec.) (isopropyl alcohol-ethyl acetate); Rf$_B$ 0.33; Rf$_C$ 0.95.

(35) H-Tyr-ala-Phe-Gly-Tyr-Val-Ser-NH$_2$.CF$_3$COOH m.p. 203°–206° C. (dec.) (diethyl ether) Rf$_C$ 0.71; E$_{1,2}$ 0.51.

(36) Boc-Tyr-ala-Phe-Gly-Tyr-Val-Ser-NH$_2$ m.p. 230° C. (dec.) (diisopropyl ether); Rf$_E$ 0.47.

(37) H-Tyr-ala-Phe-Gly-Tyr-Ser-NH$_2$.CF$_3$COOH m.p. 180°–190° C. (dec.) (diethyl ether); Rf$_C$ 0.51; Rf$_D$ 0.73; E$_{1,2}$ 0.52.

(38) Boc-Tyr-ala-Phe-Gly-Tyr-Gly-Ser-NH$_2$ m.p. 245°–250° C. (dec.) (diethyl ether-petroleum ether); Rf$_C$ 0.79.

(39) H-Tyr-ala-Phe-Gly-Phe-Pro-Ser-NH$_2$.HCl m.p. 190°–195° C. (dec.) (methyl alcohol-diethyl ether); Rf$_D$ 0.84; E$_{1,2}$ 0.52.

(40) Boc-Tyr-ala-Phe-Gly-Phe-Pro-Ser-NH$_2$ m.p. 155°–160° C. (dec.) (methyl alcohol-ethyl acetate); Rf$_B$ 0.16; Rf$_C$ 0.80.

(41) H-Tyr-ala-Phe-Gly-Phe-Hyp-Ser-NH$_2$.HCl m.p. <300° C. (dec.) (methyl alcohol-ethyl acetate) Rf$_C$ 0.47; Rf$_D$ 0.75; E$_{1,2}$ 0.51.

(42) H-Tyr-ala-Phe-Gly-Phe-Hyp-Ser(Bzl)-NH$_2$.HCl m.p. 160°–170° C. (dec.) (isopropyl alcohol-ethyl acetate); Rf$_C$ 0.65; E$_{1,2}$ 0.50.

(43) Boc-Tyr-ala-Phe-Gly-Phe-Hyp-Ser-NH$_2$ m.p. 165°–170° C. (dec.) (methyl alcohol-diethyl ether); Rf$_C$ 0.75.

(44) Boc-Tyr-ala-Phe-Gly-Phe-Hyp-Ser (Bzl)-NH$_2$ m.p. 140°–145° C. (dec.) (isopropyl alcohol-ethyl acetate); Rf$_B$ 0.25; Rf$_C$ 0.90.

(45) H-Tyr-ala-Phe-Gly-Trp-Pro-Ser-NH$_2$.HCl m.p. 210°–220° C. (dec.) (isopropyl alcohol-ethyl acetate); Rf$_C$ 0.54; Rf$_D$ 0.79; E$_{1,2}$ 0.50.

(46) Boc-Tyr-ala-Phe-Gly-Trp-Pro-Ser-NH$_2$ m.p. 175°–180° C. (dec.) (methyl alcohol-ethyl acetate); Rf$_B$ 0.12; Rf$_C$ 0.81; Rf$_D$ 0.86.

(47) H-Tyr-ala-Phe-Phe-Tyr-Pro-Ser-NH$_2$.HCl m.p. 195°–200° C. (dec.) (diethyl ether): Rf$_C$ 0.66; Rf$_D$ 0.82; E$_{1,2}$ 0.50.

(48) H-Tyr-ala-Phe-Phe-Tyr (Bzl)-Pro-Ser-NH$_2$.HCl m.p. 160°–180° C. (dec.) (ethyl alcohol-diethyl ether); Rf$_C$ 0.72; Rf$_D$ 0.90; E$_{1,2}$ 0.46.

(49) Boc-Tyr-ala-Phe-Phe-Tyr-Pro-Ser-NH$_2$ m.p. 140°–145° C. (diethyl ether); Rf$_B$ 0.18; Rf$_C$ 0.88.

EXAMPLE 6

Preparation of H-Tyr-ala-Phe-Gly-Tyr-Pro-Ser-NH-NH-Z.Hcl (63)

Step 1. Boc-Ser-NH-NH-Z (50)

To a solution of 1.0 g (4.87 mmoles) Boc-Ser-OH in 20 ml anhydrous tetrahydrofuran, 0.55 ml (4.87 mmoles) N-methylmorpholine, and 0.49 ml (4.87 mmoles) ethyl chloroformate are successively added at a temperature of −12° C. After stirring at this temperature for 2 minutes, a cold solution of 1.0 g (4.87 mmoles) H$_2$N-NH-Z.Hcl and .55 ml (4.87 mmoles) N-methylmorpholine in 20 ml dimethylformamide is added. The reaction mixture is stirred at −10° C. for 3 hours and at 20° C. for 1 hour, then filtered from salts and evaporated in vacuo. The residue is dissolved in ethyl acetate and washed several times successively with a NaCl-saturated solution of 1 M citric acid, 1 M NaHCO$_3$, and water. The organic layer is dried over anhydrous Na$_2$SO$_4$ and the solvent removed in vacuo. The product is purified by column chromatography on silica gel eluted with CHCl$_3$:MeOH=98:2. The homogeneous fractions on TLC are collected and the solvent removed in vacuo. By grinding with diethyl ether-petroleum ether, 1.4 g of compound (50) are obtained: m.p. 42°–46° C.; $[\alpha]_D^{25}$ −25.8° (c=1, MeOH); Rf$_A$=0.52.

Step 2. H-Ser-NH-NH-Z.HCl (51)

1.0 g (2.83 mmoles) Boc-Ser-NH-NH-Z (50) is dissolved in 10 ml of a 4 N solution of hydrogen chloride in anhydrous tetrahydrofuran at room temperature. After maintaining the solution for 30 minutes at room temperature, diethylether is added to the solution and the precipitate is filtered. The crude product is recrystallized from absolute ethanol-diethyl ether: there is obtained 0.7 g of compound (51): m.p. 110°–115° C.; $[\alpha]_D^{25}+20.7°$ (c=1, MeOH); $Rf_C=0.49$; $E_{1.2}=1.16$.

Step 3.  (52)

1.0 g (8.7 mmoles) H-Pro-OH is dissolved at room temperature in 4.35 ml of 2 N NaOH. The solution is then cooled to 0° C., diluted with 10 ml dimethylformamide, and the solvents removed in vacuo at 35° C. The residue is suspended in 10 ml dimethylformamide and 4.3 g (8.7 mmoles)

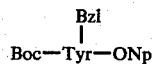

are added. The reaction mixture is stirred for 1 hour at room temperature and then evaporated in vacuo. The residue is dissolved in water and washed several times with ethyl acetate. The aqueous layer is cooled at 0° C., acidified with a 5 N aqueous solution of hydrogen chloride to pH 2, and then extracted with ethyl acetate. The organic layer is washed to neutrality with NaCl-saturated aqueous solution and dried over anhydrous $Na_2SO_4$. Removal of the solvent at 30° C. gives 3.7 g of (52), m.p. 97°–100° C. (dec.) $[\alpha]_D^{25}-15.7°$ (c=1, MeOH); $Rf_A=0.70$; $E_{5.8}=0.35$.

Step 4. Boc-Tyr-Pro-OH (53)

1.0 g (2.13 mmoles)

in 15 ml methanol is hydrogenated at 30° C. in the presence of 0.27 g 10% Pd/C. The catalyst is removed by filtration, the solution is diluted with ethyl acetate and concentrated in vacuo up to precipitation. 0.7 g of compound (53) is obtained, m.p. 136°–138° C.; $[\alpha]_D^{25}-25.0°$ (c=1, MeOH); $Rf_A=0.42$; $E_{5.8}=0.52$.

Step 5. Boc-Tyr-Pro-Ser-NH-NH-Z (54)

Starting from 1.0 g (2.65 mmoles) Boc-Tyr-Pro-OH (53) and 0.77 g (2.65 mmoles) H-Ser-NH-NH-Z.HCl (51) and operating as in Step 1, 1.46 g (54) are obtained (crystallization from diethyl ether-petroleum ether); m.p. 116°–118° C.; $[\alpha]_D^{25}-46.5°$ (c=1, MeOH); $Rf_A=0.17$, $Rf_B=0.37$.

Step 6. H-Tyr-Pro-Ser-NH-NH-Z.HCl (55)

Starting from 1.0 g (1.63 mmoles) Boc-Tyr-Pro-Ser-NH-NH-Z (54) and operating as in Step 2, 0.78 g of (55) are obtained from diethyl ether: m.p. 172°–174° C.; $[\alpha]_D^{25}-38.4°$ (c=1, MeOH); $Rf_C=0.46$; $E_{1.2}=0.79$.

Step 7. Boc-Phe-Gly-NH-NH-Z (56)

Starting from 1.0 g (3.8 mmoles) Boc-Phe-OH and 0.95 g (3.7 mmoles) H-Gly-NH-NH-Z.HCl (K. Hofmann et al., J. Am. Chem. Soc. 94, 6171, 1972) and operating as in Step 1, compound (56) (1.4 g) is recovered from methanol-diisopropyl ether: m.p. 143° C. $[\alpha]_D^{25}+5.6°$ (c=1, MeOH); $Rf_A=0.63$.

Step 8. H-Phe-Gly-NH-NH-Z.HCl (57)

1.0 g (2.1 mmoles) Boc-Phe-Gly-NH-NH-Z (56) is treated for 30 minutes at room temperature with 10 ml of a 1.3 N solution of hydrogen chloride in glacial acetic acid. Removal of the solvent in vacuo at 30° C., and grinding of the residue with diethyl ether gives 0.89 g of (57), m.p. 178° C.; $[\alpha]_D^{25}+45°$ (c=1, MeOH); $Rf_C=0.78$; $E_{1.2}=0.88$.

Step 9. Boc-ala-Phe-Gly-NH-NH-Z (58)

Starting from 1.0 g (5.3 mmoles) Boc-ala-OH and 2.09 g (5.1 mmoles) H-Phe-Gly-NH-NH-Z.HCl (57), and operating as in Step 5, compound (58) (2.5 g) is obtained from methanol-diisopropyl ether: m.p. 165° C.; $[\alpha]_D^{25}=+8°$ (c=1, MeOH); $Rf_A=0.51$.

Step 10. H-ala-Phe-Gly-NH-NH-Z.HCl (59)

Starting from 1.0 g (1.8 mmoles) Boc-ala-Phe-Gly-NH-NH-Z (58) and operating as in Step 6, 0.84 g of (59) are obtained: m.p. 180° C.; $[\alpha]_D^{25}=+0.2°$ (c=1, MeOH); $Rf_C=0.75$; $E_{1.2}=0.80$.

Step 11. Boc-Tyr-ala-Phe-Gly-NH-NH-Z (60)

Starting from 1.0 g (3.5 mmoles) Boc-Tyr-OH and 1.65 g (3.4 mmoles) H-ala-Phe-Gly-NH-NH-Z.HCl (59) and operating as in Step 5, 2.24 g of (60) are obtained (crystallization from methanol-diisopropyl ether); m.p. 148° C.; $[\alpha]_D^{25}+16.2°$ (c=1, MeOH); $Rf_A=0.38$.

Step 12. Boc-Tyr-ala-Phe-Gly-NH-NH$_2$ (61)

1.0 g (1.4 mmoles) Boc-Tyr-ala-Phe-Gly-NH-NH-Z (60) in 10 ml methanol is hydrogenated at room temperature in the presence of 0.27 g 10% Pd/C. Operating as in Step 4, 0.64 g of compound (61) is obtained, m.p. 148° C.; $[\alpha]_D^{25}+26.6°$ (c=1, MeOH); $Rf_B=0.34$; $E_{1.2}=0.57$.

Step 13. Boc-Tyr-ala-Phe-Gly-Tyr-Pro-Ser-NH-NH-Z (62)

To a solution of 1 g (1.75 mmoles) Boc-Tyr-ala-Phe-Gly-NH-NH$_2$ (61) in 15 ml anhydrous dimethylformamide, 1.1 ml (4.38 mmoles) 4 N hydrogen chloride in anhydrous tetrahydrofuran and 0.2 ml (1.93 mmoles) n-butyl nitrite are successively added at a temperature of −30° C. After stirring at this temperature for 30 minutes, 0.5 ml (4.38 mmoles) N-methylmorpholine are added, followed by a cold solution (−30° C.) of 0.803 g (1.46 mmoles) H-Tyr-Pro-Ser-NH-NH-Z.HCl (55) and 0.16 ml (1.46 mmoles) N-methyl-morpholine in 15 ml anhydrous dimethylformamide. The reaction mixture is allowed to react at −9° C. for two days; then the salts are filtered off, the solvent is removed in vacuo, and the product is poured into a 10% citric acid solution cooled at 0° C. The precipitate is filtered, washed to neutrality with water and dried in vacuo. The product is recrystallized from ethyl acetate-diethyl ether; 1.15 g of (62) are obtained: m.p. 140°–150° C.; $[\alpha]_D^{25}-20.3°$ (c=1, MeOH); $Rf_B=0.17$, $Rf_C=0.92$.

Step 14.
H-Tyr-ala-Phe-Gly-Tyr-Pro-Ser-NH-NH-Z.HCl (63)

Starting from 1.0 g (0.95 mmoles) Boc-Tyr-ala-Phe-Gly-Tyr-Pro-Ser-NH-NH-Z (62) and operating as in Step 2, 0.89 g of compound (63) are obtained from ethyl acetate; m.p. 170° C. (dec.); $[\alpha]_D^{25}+1.8°$ (c=1, MeOH); $[\alpha]_D^{25}+1.0°$ (c=1, AcOH); Rf$_C$=0.69; E$_{1,2}$=0.50.

EXAMPLE 7

Preparation of H-Tyr-ala-Phe-Gly-Tyr-NH-NH-Z.HCl (67)

Step 1. Boc-Tyr-NH-NH-Z (64)

To a solution of 1.0 g (3.55 mmoles) Boc-Tyr-OH in 20 ml anhydrous tetrahydrofuran, 0.4 ml (3.55 mmoles) N-methylmorpholine, and 0.48 ml (3.55 mmoles) isobutyl chloroformate are successively added at a temperature of −12° C. After stirring at this temperature for 2 minutes, a cold solution of 0.72 g (3.55 mmoles) H$_2$N-NH-Z.HCl and 0.4 ml N-methyl morpholine in 20 ml dimethylformamide is added. The reaction mixture is stirred at −10° C. for 90 minutes, then filtered from salts, and evaporated in vacuo. The residue is dissolved in ethyl acetate and washed several times successively with an aqueous solution of 1 M citric acid, 1 M NaHCO$_3$, and saturated NaCl. The organic layer is dried over anhydrous Na$_2$SO$_4$, and removal of the solvent gives 1.3 g of compound (64): m.p. 68°–70° C.; $[\alpha]_D^{25}-5.85$ (c=2, MeOH); Rf$_A$=0.76.

Step 2. H-Tyr-NH-NH-Z.HCl (65)

1.0 g (2.33 mmoles) Boc-Tyr-NH-NH-Z (64) is dissolved in 10 ml of 4 N solution of hydrogen chloride in anhydrous tetrahydrofuran at room temperature. After 30 minutes at room temperature the solvent is evaporated in vacuo and the product is precipitated from isopropyl alcohol-diethylether; 0.76 g of compound (65) are obtained: m.p. 103°–105° C.; $[\alpha]_D^{25}+48.8°$ (c=1, MeOH); Rf$_C$=0.70; E$_{1,2}$=0.92.

Step 3. Boc-Tyr-ala-Phe-Gly-Tyr-NH-NH-Z (66)

To a solution of 1.0 g (1.75 mmoles) Boc-Tyr-ala-Phe-Gly-NH-NH$_2$ (61) in 15 ml anhydrous dimethylformamide, 1.1 ml (4.38 mmoles) 4 N hydrogen chloride in anhydrous tetrahydrofuran and 0.2 ml (1.93 mmoles) N-butyl nitrite are successively added at a temperature of −30° C. After stirring at this temperature for 30 minutes, 0.5 ml (4.38 mmoles) N-methylmorpholine are added, followed by a cold solution (−30° C.) of 0.535 g (1.46 mmoles) H-Tyr-NH-NH-Z.HCl (65) and 0.16 ml (1.46 mmoles) N-methylmorpholine in 15 ml anhydrous dimethylformamide. The reaction mixture is allowed to react at −9° C. for three days, then the salts are filtered off, the solvent is removed in vacuo, and the product is poured into 10% citric acid aqueous solution cooled to 0° C. The precipitate is filtered, washed to neutrality with water and dried in vacuo. The product is recrystallized from isopropyl alcohol-diethyl ether; 0.85 g of compound (66) are obtained, m.p. 137°–150° C.; $[\alpha]_D^{25}+3.8°$ (c=1, MeOH); Rf$_A$=0.27; Rf$_B$=0.52.

Step 4. H-Tyr-ala-Phe-Gly-Tyr-NH-NH-Z.HCl (67)

Starting from 1.0 g (1.15 mmoles) Boc-Tyr-ala-Phe-Gly-Tyr-NH-NH-Z (66) and operating as in Step 2, compound (67) (0.83 g) is obtained from ethyl acetate: m.p. 190° C. (dec.); $[\alpha]_D^{25}+19.9°$ (c=1, MeOH); Rf$_C$=0.81; E$_{1,2}$=0.59.

EXAMPLE 8

Preparation of H-Tyr-ala-Phe-Gly-NH-NH-Z.HCl (68)

Starting from 1.0 g (1.60 mmoles) Boc-Tyr-ala-Phe-Gly-NH-NH-Z (60), and operating as in Step 8 of Example 6, 0.70 g of compound (68) are obtained from ethyl acetate, m.p. 215° C.; $[\alpha]_D^{23}+33.0°$ (c=1, MeOH); Rf$_C$=0.70; E$_{1,2}$=0.62.

EXAMPLE 9

Preparation of H-Tyr-ala-Phe-Gly-NH-NH-CO-CH$_2$-CH$_2$-CH$_3$.HCl (70)

Step 1. Boc-Tyr-ala-Phe-Gly-NH-NH-CO-CH$_2$-CH$_2$-CH$_3$ (69)

Starting from 0.12 ml (1.3 mmoles) butyric acid and 0.742 g (1.3 mmoles) Boc-Tyr-ala-Phe-Gly-NH-NH$_2$ (61), and operating as in Step 1 of Example 6, 0.8 g of compound (69) are obtained from ethyl acetate; m.p. 125° C. (dec.), $[\alpha]_D^{25}+18.3°$ (c=1, MeOH); Rf$_C$=0.37.

Step 2. H-Tyr-ala-Phe-Gly-NH-NH-CO-CH$_2$-CH$_2$-CH$_3$.HCl (70)

Starting from 1.0 g (1.46 mmoles) Boc-Tyr-ala-Phe-Gly-NH-NH-CO-CH$_2$-CH$_2$-C$_3$ (69) and operating as in Step 2 of Example 6, after purification by column chromatography on silica gel and eluting with chloroform-methanol=9:1, 0.58 g of compound (70) are obtained from isopropyl alcohol-diethyl ether; m.p. 215°–218° C. (dec.) $[\alpha]_D^{25}+40.1°$ (c=1, MeOH); Rf$_C$=0.67, Rf$_D$=0.84; $_{1,2}$=0.75.

EXAMPLE 10

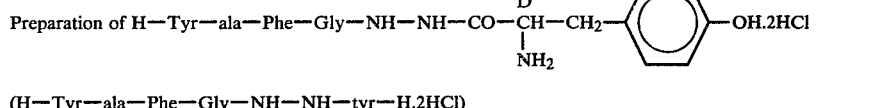

Preparation of 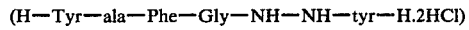

(H—Tyr—ala—Phe—Gly—NH—NH—tyr—H.2HCl)

Step 1. Boc-Tyr-ala-Phe-Gly-NH-NH-tyr-Boc (71)

Starting from 1.0 (3.55 mmoles) Boc-tyr-OH and 2.03 g (3.55 mmoles) Boc-Tyr-ala-Phe-Gly-NH-NH$_2$ (60), and operating as in Step 1 of Example 6, 2.3 g of compound (71) is obtained from ethyl acetate; m.p. 145°–150° C.; $[\alpha]_D^{25}+14.8°$ (c=1, MeOH); Rf$_A$=0.26 Rf$_B$=0.39.

Step 2. H-Tyr-ala-Phe-Gly-NH-NH-tyr-H.HCl (72)

Starting from 1.0 g (1.2 mmoles) Boc-Tyr-ala-Phe-Gly-NH-NH-tyr-Boc (71), and operating as in Step 2 of Example 6, 0.760 g of compound (72) are obtained from diethyl ether; m.p. 210°–215° C. (dec.); $[\alpha]_D^{25}+13.5°$ (c=1, MeOH); Rf$_C$=0.48; E$_{1,2}$=0.84.

By the classical solution procedure the following derivatives have been synthesized also:

(73) H-Tyr-ala-Phe-Gly-tyr-NHNH$_2$.2HCl m.p. 150°–155° C. (dec.) (ethyl acetate); Rf$_C$=0.70
(74) Boc-Tyr-ala-Phe-Sar-NH-NH-Z
(75) H-Tyr-ala-Phe-Sar-Tyr-NH-NH-Z.HCl
(76) Boc-Tyr-ala-Phe-Sar-Tyr-NH-NH-Z

(77) H-Tyr-ala-Phe-Sar-Tyr-NH-NH-Boc.HCl
(78) Tfa-Tyr-ala-Phe-Sar-Tyr-NH-NH-Boc
(79) H-Tyr-ala-Phe-Gly-Tyr-NH-NH-Ph.HCl
(80) Boc-Tyr-ala-Phe-Gly-Tyr-NH-NH-Ph
(81) H-Tyr-ala-Phe-Gly-Tyr-NH-NH-Boc.HCl
(82) Tfa-Tyr-ala-Phe-Gly-Tyr-NH-NH-Boc
(83) H-Tyr-ala-Phe-Gly-Tyr-NH-NH-Adoc.HCl
(84) Tfa-Tyr-ala-Phe-Gly-Tyr-NH-NH-Adoc
(85) H-Tyr-ala-Phe-Gly-Tyr-NH-NH-Ad.HCl
(86) Boc-Tyr-ala-Phe-Gly-Tyr-NH-NH-Ad
(87) H-Tyr-ala-Phe-Gly-Leu-NH$_2$.HCl m.p. 143°–147° C. (isopropyl alcohol-diethyl ether); $[\alpha]_D^{28}$ +8.1° (c=1, MeOH); Rf$_C$ 0.73; E$_{1.2}$ 0.62.
(88) H-Tyr-ala-Phe-Gly-Met-NH$_2$.HCl m.p. 220°0225° C. (isopropyl alcohol-diisopropyl ether); $[\alpha]_D^{23}$ +13.5° (c=1, MeOH); Rf$_C$ 0.68; E$_{1.2}$ 0.63.
(89) H-Tyr-ala-Phe-Sar-Tyr-Pro-Ser-NH$_2$.HCl m.p. 195°–200° C. (dec.) (diethyl ether); Rf$_C$ 0.49; E$_{1.2}$ 0.49; $[\alpha]_D^{23}$ +18.0° (c=1, MeOH).
(90) H-Tyr-ala-Phe-Gly-Gly-Pro-Ser-NH$_2$.HCl m.p. 180° C. (dec.) (diethyl ether); $[\alpha]_D^{20}$ 0 (c=1, MeOH); Rf$_C$ 0.32; E$_{1.2}$ 0.58.
(91) H-Tyr-ala-Phe-Gly-Tyr-Pro-Ser-NHMe. HCl m.p. 240° C. (dec.) (diethyl ether); $[\alpha]_D^{28}$ 0 (c=1, MeOH); Rf$_C$ 0.55; E$_{1.2}$ 0.52.
(92) H-Tyr-ala-Phe-Gly-Tyr-Pro-Ser-NHEt. HCl m.p. 235° (dec.) (diethyl ether); $[\alpha]_D^{28}$ −3.54° (c=1, MeOH); Rf$_C$ 0.62; E$_{1.2}$ 0.52.
(93) H-Tyr-ala-Phe-Gly-Tyr-Pro-Ser-Ome. HCl m.p. 240° C. (dec.) (diethyl ether); $[\alpha]_D^{28}$ −4.5° (c=1, MeOH); Rf$_C$ 0.66; E$_{1.2}$ 0.55.
(94) H-Tyr-met-Phe-Gly-NHNHZ. HCl m.p. 140°–143° C. (CHCl$_3$/diethyl ether); $[\alpha]_D^{28}$ −21.6° (c=1, DMF); Rf$_C$ 0.79; E$_{1.2}$ 0.54.
(95) H-Tyr-met(O)-Phe-Gly-NHNHZ. HCl m.p. 115°–120° C. (CHCl$_3$/diethyl ether); $[\alpha]_D^{28}$ −23.2° (c=1, DMF); Rf$_C$ 0.69; E$_{1.2}$ 0.53.
(96) H-Tyr-ala-Phe-Gly-NHNHLrl. HCl m.p. 191°–198° C. (dec.) (isopropyl alcohol-diethyl ether); $[\alpha]_D^{23}$ +46.0° (c=1, MeOH); Rf$_C$ 0.84; E$_{1.2}$ 0.41.
(97) H-Tyr-ala-Phe-Gly-NHNHBnl. HCl m.p. 254°–258° C. (dec.) (CH$_3$OH/CHCl$_3$/ethyl acetate); $[\alpha]_D^{26}$ +41.4 (c=1, MeOH); Rf$_C$ 0.79; E$_{1.2}$ 0. 63.
(98) H-Tyr-ala-Phe-Gly-NHNH Adoc m.p. 142°–144° C. (dec.) (isopropyl alcohol/diethyl ether); $[\alpha]_D^{23}$ +20.7 (c=1, MeOH); Rf$_C$ 0.78; E$_{1.2}$ 0.47.
(99) H-Tyr-ala-Phe-Gly-NHNHBoc m.p. 154° C. (dec.) (diethyl ether); Rf$_C$ 0.79; E$_{1.2}$ 0.60; $[\alpha]_D^{23}$ +27.9 (C=1, MeOH).
(100) H-Tyr-ala-Phe-Gly-Pro-NH$_2$. HCl
(101) H-Tyr-ala-Phe-Gly-Ser-NH$_2$. HCl
(102) H-Tyr-ala-Phe-Gly-tyr-NH$_2$. HCl
(103) H-Tyr-ala-Phe-Sar-Tyr-NH$_2$. HCl
(104) H-Tyr-met-Phe-Gly-Tyr-NH$_2$. HCl
(105) H-Tyr-met-Phe-Gly-Tyr-Pro-Ser-NH$_2$. HCl
(106) H-Tyr-ala-Phe-Pro-Tyr-Pro-Ser-NH$_2$. HCl
(107) H-Tyr-ala-Phe-MePhe-Tyr-Pro-Ser-NH$_2$. HCl
(108) H-Tyr-ala-Phe-MePhe-Tyr-Pro-Ser-OMe. HCl
(109) H-Tyr-ala-Phe-Gly-Tyr-Ppa-Ser-NH$_2$. HCl
(110) H-Tyr-ala-Phe-Gly-Tyr-Aze-Ser-NH$_2$. HCl
(111) H-Tyr-ala-Phe-Gly-Tyr-Tia-Ser-NH$_2$. HCl
(112) H-Tyr-ala-Phe-Gly-Tyr-ΔPr-Ser-NH$_2$. HCl
(113) H-Tyr-ala-Phe-Gly-Phe(NO$_2$)-Pro-Ser-NH$_2$. HCl
(114) H-Tyr-ala-Phe-Gly-Tyr-Pro-Abu-NH$_2$. HCl
(115) H-Tyr-ala-Phe-Gly-Tyr-Pro-Gly-NH$_2$. HCl
(116) H-Tyr-ala-Phe-Gly-Tyr(Bzl)-Pro-Ser(Bzl)-NH$_2$. HCl
(117) H-Tyr-ala-Phe-Gly-Tyr-Pro-Ser(Bzl)-NH$_2$. HCl
(118) H-Tyr-ala-Phe-Gly-Tyr-NH-Ad. HCl
(119) H-Tyr-ala-Phe-Gly-Tyr-Pro-Ser-OH. HCl
(120) H-Tyr-ala-Phe-Gly-Tyr-NH-CH$_2$CF$_3$. HCl
(121) H-Tyr-met-Phe-Gly-NHNH$_2$. HCl
(122) H-Tyr-ala-Phe-Gly-tyr-NHNHZ. HCl
(123) H-Tyr-ala-Phe-Sar-Tyr-NHNHZ. HCl In the above formulae
Me=CH$_3$,
Et=CH$_2$CH$_3$,
Z=benzyloxycarbonyl,
Lrl=lauryl,
Bnl=benzoyl, and
Bzl=benzyl.

(124) H-Tyr-ala-Phe-Gly-Tyr-3allo Hyp-Ser-NH$_2$
(125) H-Tyr-ala-Phe-Gly-Pro-Ser-NH$_2$
(126) H-Tyr-ala-Phe-Gly-Tyr-Pro-Ser-NH-NH$_2$
(127) H-Tyr-ala-Phe-Gly-Met(O)-NH$_2$
(128) H-Tyr-ala-Phe-Gly-Nva-NH$_2$
(129) H-Tyr-met-Phe-Gly-Pro-NH$_2$
(130) H-Tyr-met-Phe-Gly-Nva-NH$_2$
(131) H-Tyr-met(O)-Phe-Gly-Tyr-Pro-Ser-NH$_2$
(132) H-Tyr-ala-Phe-Ser-Tyr-Hyp-Ser-NH$_2$
(133) H-Tyr-ala-Phe-Sar-Tyr(Bzl)-Hyp-Ser(Bzl)-NH$_2$
(134) H-Tyr-ala-Phe-Gly-Tyr(Bzl)-Ppa-Ser-NH$_2$
(135) H-Tyr-ala-Phe-Gly-Tyr-alloHyp-Ser-NH$_2$
(136) H-Tyr-ala-Phe-Gly-Tyr-3Hyp-Ser-NH$_2$
(137) H-Tyr-ala-Phe-Gly-Tyr(Bzl)-3Hyp-Ser(Bzl)-NH$_2$
(138) H-Tyr-ala-Phe-Gly-Tyr(Bzl)-Aze-Ser-NH$_2$
(139) H-Tyr-ala-Phe-Gly-Tyr(Bzl)-Tia-Ser-NH$_2$
(140) H-Tyr-ala-Phe-Gly-Tyr(Bzl)-ΔPr-Ser-NH$_2$
(141) H-Tyr-ala-Phe-Gly-Tyr-βAla-Ser-NH$_2$
(142) H-Tyr-ala-Phe-Gly-Phe(F)-Pro-Ser-NH$_2$
(143) H-Tyr-ala-Phe-Gly-Cha-Pro-Ser-NH$_2$
(144) H-Tyr-ala-Phe-Gly-Phg-Pro-Ser-NH$_2$
(145) H-Tyr-ala-Phe-Gly-Tyr (Me)-Pro-Ser-NH$_2$
(146) H-Tyr-ala-Phe-Gly-Tyr-Pro-Ser-NH-CH(CH$_3$)$_2$
(147) H-Tyr-met(O)-Phe-Gly-NHNH$_2$
(148) H-Tyr-ala-Phe-Sar-Tyr-NHNH$_2$
(149) H-Tyr-ala-Phe-Phe-NH-NH-Z
(150) H-Tyr-ala-Phe-Phe-NH-NH$_2$
(151) H-Tyr-ala-Phe-Gly-Sar-Ser-NH$_2$
(152) Boc-Tyr-ala-Phe-Sar-NH-NH-Z
(153) H-Tyr-ala-Phe-Gly-Tyr-NH-NH$_2$
(154) H-Tyr-ala-Phe-Gly-Leu-NH-NH-Z
(155) H-Tyr-ala-Phe-Gly-Leu-NH-NH$_2$
(156) H-Tyr-ala-Phe-Gly-Tyr(Me)-Hyp-Ser-NH$_2$
(157) H-Tyr-ala-Phe-MePhe-Tyr-Pro-Ser-NH$_2$
(158) H-Tyr-ala-Phe-Gly-Tyr-MeAla-Ser-NH$_2$
(159) H-Tyr-ala-Phe-Tyr(Bzl)-alloHyp-Ser(Bzl)-NH$_2$
(160) H-Tyr-ala-Phe-MePhe-Tyr-Pro-Ser-OH
(161) H-Tyr-ala-Phe-Sar-Tyr(Bzl)-Pro-Ser-NH$_2$
(162) H-Tyr-ala-Phe-Pro-Tyr(Bzl)-Pro-Ser-NH$_2$
(163) H-Tyr-ala-Phe-Pro-Tyr-Hyp-Ser-NH$_2$
(164) H-Tyr-ala-Phe-Pro-Tyr(Bzl)-Hyp-Ser(Bzl)-NH$_2$ In the above formulae,
Cha=hexahydrophenylalanine, Phg=phenylglycine,
Phe(F)=p-fluorophenylalanine,
met(O)=D-methionine sulphoxide,
MePhe=N-methylphenylalanine,
Ppa=pipecolic acid,
Aze=2-azetidine carboxylic acid,
Tia=4-tiazolidine carboxylic acid,
ΔPr=

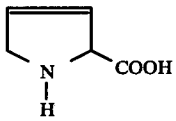

Phe(NO₂)=p-nitro-phenylalanine,
Abu=α-amino-n-butyric acid,
Tyr(Bzl)-tyrosine O-benzyl ether, and
Ser(Bzl)-serine O-benzyl ether.

All of the listed compounds were synthesized either by the classical solution procedure or by the solid phase.

What is claimed is:

1. A biologically active peptide selected from the group consisting of
H-Tyr-ala-Phe-Gly-Tyr-Pro-Ser-NH₂,
H-Tyr-ala-Phe-Gly-Tyr-NH₂,
H-Tyr-ala-Phe-Gly-OMe,
H-Tyr-ala-Phe-Gly-OH,
H-Tyr-ala-Phe-Gly-NH₂,
H-Tyr-ala-Phe-Gly-NH-NH₂,
H-Tyr-ala-Phe-Sar-NH-NH₂,
H-Tyr-ala-Phe-Sar-NH-NH-Z,
Boc-Tyr-ala-Phe-Sar-NH-NH₂,
Boc-Tyr-ala-Phe-Phe-NH-NH₂,
H-Tyr-ala-Phe-Gly-Tyr-Pro-NH₂,
H-Tyr-ala-Phe-Gly(Bzl)-Pro-NH₂,
Boc-Tyr-ala-Phe-Gly-Tyr-Pro-NH₂,
Boc-Tyr-ala-Phe-Gly-Tyr(Bzl)-Pro-NH₂,
H-Tyr-ala-Phe-Gly-Tyr-Ser-NH₂,
Boc-Tyr-ala-Phe-Gly-Tyr-Ser-NH₂,
H-Tyr-ala-Phe-Gly-Tyr-Hyp-Ser-NH₂,
H-Tyr-ala-Phe-Gly-Tyr(Bzl)-Hyp-Ser(Bzl)-NH₂,
Boc-Tyr-ala-Phe-Gly-Tyr-Hyp-Ser-NH₂,
Boc-Tyr-ala-Phe-Gly-Tyr(Bzl)-Hyp-Ser(Bzl)-NH₂,
H-Tyr-ala-Phe-Gly-Tyr-Val-Ser-NH₂,
Boc-Tyr-ala-Phe-Gly-Tyr-Val-Ser-NH₂,
H-Tyr-ala-Phe-Gly-Tyr-Gly-Ser-NH₂,
Boc-Tyr-ala-Phe-Gly-Tyr-Gly-Ser-NH₂,
H-Tyr-ala-Phe-Gly-Phe-Pro-Ser-NH₂,
Boc-Tyr-ala-Phe-Gly-Phe-Pro-Ser-NH₂,
H-Tyr-ala-Phe-Gly-Phe-Hyp-Ser-NH₂,
H-Tyr-ala-Phe-Gly-Phe-Hyp-Ser(Bzl)-NH₂,
Boc-Tyr-ala-Phe-Gly-Phe-Hyp-Ser-NH₂,
Boc-Tyr-ala-Phe-Gly-Phe-Hyp-Ser(Bzl)-NH₂,
H-Tyr-ala-Phe-Gly-Trp-Pro-Ser-NH₂,
Boc-Tyr-ala-Phe-Gly-Trp-Pro-Ser-NH₂,
H-Tyr-ala-Phe-Phe-Tyr-Pro-Ser-NH₂,
H-Tyr-ala-Phe-Phe-Tyr(Bzl)-Pro-Ser-NH₂,
Boc-Tyr-ala-Phe-Phe-Tyr-Pro-Ser-NH₂,
H-Tyr-ala-Phe-Gly-Tyr-Pro-Ser-NH-NH-Z,
H-Tyr-ala-Phe-Gly-Tyr-NH-NH-Z,
H-Tyr-ala-Phe-Gly-NH-NH-Z,
H-Tyr-ala-Phe-Gly-NH-NH-CO-CH₂-CH₂-CH₃,
H-Tyr-ala-Phe-Gly-NH-NH-tyr-H,
H-Tyr-ala-Phe-Sar-NH-NH-Z,
Boc-Tyr-ala-Phe-Sar-NH-NH-Z,
H-Tyr-ala-Phe-Sar-Tyr-NH-NH-Z,
Boc-Tyr-ala-Phe-Sar-Tyr-NH-NH-Z,
H-Tyr-ala-Phe-Sar-Tyr-NH-NH-Boc,
Tfa-Tyr-ala-Phe-Sar-Tyr-NH-NH-Boc,
H-Tyr-ala-Phe-Gly-Tyr-NH-NH-Ph,
Boc-Tyr-ala-Phe-Gly-NH-NH-Ph,
H-Tyr-ala-Phe-Gly-Tyr-NH-NH-Boc,
Tfa-Tyr-ala-Phe-Gly-Tyr-NH-NH-Boc,
H-Tyr-ala-Phe-Gly-Tyr-NH-NH-Adoc,
Tfa-Tyr-ala-Phe-Gly-Tyr-NH-NH-Adoc,
H-Tyr-ala-Phe-Gly-Tyr-NH-NH-Ad,
Boc-Tyr-ala-Phe-gly-NH-NH-Ad,
H-Tyr-ala-Phe-Gly-Leu-NH₂,
H-Tyr-ala-Phe-Gly-Met-NH₂,
H-Tyr-ala-Phe-Sar-Tyr-Pro-Ser-NH₂,
H-Tyr-ala-Phe-Gly-Gly-Pro-Ser-NH₂,
H-Tyr-ala-Phe-Gly-Tyr-Pro-Ser-NHMe,
H-Tyr-ala-Phe-Gly-Tyr-Pro-Ser-NHEt,
H-Tyr-ala-Phe-Gly-Tyr-Pro-Ser-OMe,
H-Tyr-met-Phe-Gly-NHNHZ,
H-Tyr-met(O)-Phe-Gly-NHNHZ,
H-Tyr-ala-Phe-Gly-NHNHLrl,
H-Tyr-ala-Phe-Gly-MHNHBnl,
H-Tyr-ala-Phe-Gly-tyrNHNH₂,
H-Tyr-ala-Phe-Gly-NHNHAdoc,
H-Tyr-ala-Phe-Gly-NHNHBoc,
H-Tyr-ala-Phe-Gly-Pro-NH₂,
H-Tyr-ala-Phe-Gly-Ser-NH₂,
H-Tyr-ala-Phe-Gly-tyr-NH₂,
H-Tyr-ala-Phe-Sar-Tyr-NH₂,
H-Tyr-ala-Phe-Gly-Tyr-Sar-Ser-NH₂
H-Tyr-ala-Phe-Gly-Pro-Ser-NH₂,
H-Tyr-ala-Phe-Gly-Tyr-Pro-Ser-NH-NH₂,
H-Tyr-met-Phe-Gly-Tyr-NH₂,
H-Tyr-met-Phe-Gly-Tyr-Pro-Ser-NH₂,
H-Tyr-ala-Phe-Pro-Tyr-Pro-Ser-NH₂,
H-Tyr-ala-Phe-MePhe-Tyr-Pro-Ser-OMe,
H-Tyr-ala-Phe-Gly-Tyr-Ppa-Ser-NH₂,
H-Tyr-ala-Phe-Gly-Tyr-Aze-Ser-NH₂,
H-Tyr-ala-Phe-Gly-Tyr-Tia-Ser-NH₂,
H-Tyr-ala-Phe-Gly-Tyr-ΔPr-Ser-NH₂,
H-Tyr-ala-Phe-Gly-Phe(NO₂)-Pro-Ser-NH₂,
H-Tyr-ala-Phe-Gly-Tyr-Pro-Abu-NH₂,
H-Tyr-ala-Phe-Tyr-Pro-Gly-NH₂,
H-Tyr-ala-Phe-Gly-Tyr(Bzl)-Pro-Ser(Bzl)-NH₂,
H-Tyr-ala-Phe-Gly-Tyr-Pro-Ser(Bzl)-NH₂,
H-Tyr-ala-Phe-Gly-Tyr-NH-Ad,
H-Tyr-ala-Phe-Gly-Tyr-Pro-Ser-OH,
H-Tyr-ala-Phe-Gly-Tyr-NH-Ch₂CF₃,
H-Tyr-ala-met-Phe-Gly-NHNH₂,
H-Tyr-ala-Phe-Gly-tyr-NHNHZ,
H-Tyr-ala-Phe-Gly-Met(O)-NH₂,
H-Tyr-ala-Phe-Gly-Nva-NH₂,
H-Tyr-met-Phe-Gly-Pro-NH₂,
H-Tyr-met-Phe-Gly-Nva-NH₂,
H-Tyr-met(O)-Phe-Gly-Tyr-Pro-Ser-NH₂,
H-Tyr-ala-Phe-Sar-Tyr-Hyp-Ser-NH₂,
H-Tyr-ala-Phe-Sar-Tyr(Bzl)-Hyp-Ser(Bzl)-NH₂,
H-Tyr-ala-Phe-Gly-Tyr(Bzl)-Ppa-Ser-NH₂,
H-Tyr-ala-Phe-Gly-Tyr-alloHyp-Ser-NH₂,
H-Tyr-ala-Phe-Gly-Tyr-3Hyp-Ser-NH₂,
H-Tyr-ala-Phe-Gly-Tyr(Bzl)-3-Hyp-Ser(Bzl)-NH₂,
H-Tyr-ala-Phe-Gly-Tyr(Bzl)-Aze-Ser-NH₂,
H-Tyr-ala-Phe-Gly-Tyr(Bzl)-Tia-Ser-NH₂,
H-Tyr-ala-Phe-Gly-Tyr(Bzl)-ΔPr-Ser-NH₂,
H-Tyr-ala-Phe-Gly-Tyr-βAla-Ser-NH₂,
H-Tyr-ala-Phe-Gly-Phe(F)-Pro-Ser-NH₂,
H-Tyr-ala-Phe-Gly-Cha-Pro-Ser-NH₂, H-Tyr-ala-Phe-Gly-Phg-Pro-Ser-NH$_2$,
H-Tyr-ala-Phe-Gly-Tyr(Me)-Pro-Ser-NH$_2$,
H-Tyr-ala-Phe-Gly-Tyr-Pro-Ser-NH-CH(CH$_3$)$_2$,
H-Tyr-met(O)-Phe-Gly-NHNH$_2$,
H-Tyr-ala-Phe-Sar-Tyr-NHNH$_2$,
H-Tyr-ala-Phe-Phe-NH-NH$_2$,
H-Tyr-ala-Phe-MePhe-Tyr-Pro-Ser-NH$_2$,
H-Tyr-ala-Phe-Gly-Tyr-MeAla-Ser-NH$_2$,
H-Tyr-ala-Phe-Phe-NH-NHZ,
H-Tyr-ala-Phe-Gly-Tyr-NH-NH$_2$,
H-Tyr-ala-Phe-Gly-Leu-NH-NHZ,
H-Tyr-ala-Phe-Gly-Tyr(Me)-Hyp-Ser-NH$_2$,
H-Tyr-ala-Phe-Tyr(Bzl)-alloHyp-Ser-(Bzl)-NH$_2$,
H-Tyr-ala-Phe-MePhe-Tyr-Pro-Ser-OH,
H-Tyr-ala-Phe-Sar-Tyr(Bzl)-Pro-Ser-NH$_2$,
H-Tyr-ala-Phe-Pro-Tyr(Bzl)-Pro-Ser-NH$_2$,
H-Tyr-ala-Phe-Pro-Tyr-Hyp-Ser-NH$_2$,
H-Tyr-ala-Phe-Pro-Tyr(Bzl)-Hyp-Ser(Bzl)-NH$_2$, and
H-Tyr-ala-Phe-Gly-Tyr-3alloHyp-Ser-NH$_2$,
and a pharmaceutically acceptable salt thereof.

2. A compound as defined in claim 1, wherein in peptide is H-Tyr-ala-Phe-Gly-Tyr-Pro-Ser-NH$_2$.

3. A compound as defined in claim 1, wherein the peptide is H-Tyr-ala-Phe-Gly-Tyr-NH$_2$.

4. A compound as defined in claim 1, wherein the peptide is H-Tyr-ala-Phe-Gly-OMe.

5. A compound as defined in claim 1, wherein the peptide is H-Tyr-ala-Phe-Gly-OH.

6. A compound as defined in claim 1, wherein the peptide is H-Tyr-ala-Phe-Gly-NH$_2$.

7. A compound as defined in claim 1, wherein the peptide is H-Tyr-ala-Phe-Gly-NH-NH$_2$.

8. A compound as defined in claim 1, wherein the peptide is H-Tyr-ala-Phe-Sar-NH-NH$_2$.

9. A compound as defined in claim 1, wherein the peptide is H-Tyr-ala-Phe-Sar-NH-NH-Z.

10. A compound as defined in claim 1, wherein the peptide is Boc-Tyr-ala-Phe-Sar-NH-NH$_2$.

11. A compound as defined in claim 1, wherein the peptide is Boc-Tyr-ala-Phe-Phe-NH-NH$_2$.

12. A compound as defined in claim 1, wherein the peptide is H-Tyr-ala-Phe-Gly-Tyr-Pro-NH$_2$.

13. A compound as defined in claim 1, wherein the peptide is H-Tyr-ala-Phe-Gly-Tyr(Bzl)-Pro-NH$_2$.

14. A compound as defined in claim 1, wherein the peptide is Boc-Tyr-ala-Phe-Gly-Tyr-Pro-NH$_2$.

15. A compound as defined in claim 1, wherein the peptide is Boc-Tyr-ala-Phe-Gly-Tyr(Bzl)-Pro-NH$_2$.

16. A compound as defined in claim 1, wherein the peptide is H-Tyr-ala-Phe-Gly-Tyr-Ser-NH$_2$.

17. A compound as defined in claim 1, wherein the peptide is Boc-Tyr-ala-Phe-Gly-Tyr-Ser-NH$_2$.

18. A compound as defined in claim 1, wherein the peptide is H-Tyr-ala-Phe-Gly-Tyr-Hyp-Ser-NH$_2$.

19. A compound as defined in claim 1, wherein the peptide is H-Tyr-ala-Phe-Gly-Tyr(Bzl)-Hyp-Ser(Bzl)-NH$_2$.

20. A compound as defined in claim 1, wherein the peptide is Boc-Tyr-ala-Phe-Gly-Tyr-Hyp-Ser-NH$_2$.

21. A compound as defined in claim 1, wherein the peptide is Boc-Tyr-ala-Phe-Gly-Tyr(Bzl)-Hyp-Ser(Bzl)-NH$_2$.

22. A compound as defined in claim 1, wherein the peptide is H-Tyr-ala-Phe-Gly-Tyr-Val-Ser-NH$_2$.

23. A compound as defined in claim 1, wherein the peptide is Boc-Tyr-ala-Phe-Gly-Tyr-Val-Ser-NH$_2$.

24. A compound as defined in claim 1, wherein the peptide is H-Tyr-ala-Phe-Gly-Tyr-Gly-Ser-NH$_2$.

25. A compound as defined in claim 1, wherein the peptide is Boc-Tyr-ala-Phe-Gly-Tyr-Gly-Ser-NH$_2$.

26. A compound as defined in claim 1, wherein the peptide is H-Tyr-ala-Phe-Gly-Phe-Pro-Ser-NH$_2$.

27. A compound as defined in claim 1, wherein the peptide is Boc-Tyr-ala-Phe-Gly-Phe-Pro-Ser-NH$_2$.

28. A compound as defined in claim 1, wherein the peptide is H-Tyr-ala-Phe-Gly-Phe-Hyp-Ser-NH$_2$.

29. A compound as defined in claim 1, wherein the peptide is H-Tyr-ala-Phe-Gly-Phe-Hyp-Ser(Bzl)-NH$_2$.

30. A compound as defined in claim 1, wherein the peptide is Boc-Tyr-ala-Phe-Gly-Phe-Hyp-Ser-NH$_2$.

31. A compound as defined in claim 1, wherein the peptide is Boc-Tyr-ala-Phe-Gly-Phe-Hyp-Ser(Bzl)-NH$_2$.

32. A compound as defined in claim 1, wherein the peptide is H-Tyr-ala-Phe-Gly-Trp-Pro-Ser-NH$_2$.

33. A compound as defined in claim 1, wherein the peptide is Boc-Tyr-ala-Phe-Gly-Trp-Pro-Ser-NH$_2$.

34. A compound as defined in claim 1, wherein the peptide is H-Tyr-ala-Phe-Phe-Tyr-Pro-Ser-NH$_2$.

35. A compound as defined in claim 1, wherein the peptide is H-Tyr-ala-Phe-Phe-Tyr(Bzl)-Pro-Ser-NH$_2$.

36. A compound as defined in claim 1, wherein the peptide is Boc-Tyr-ala-Phe-Phe-Tyr-Pro-Ser-NH$_2$.

37. The compound of claim 1, wherein said peptide is H-Tyr-ala-Phe-Gly-Tyr-Pro-Ser-NH-NH-Z.

38. The compound of claim 1, wherein said peptide is H-Tyr-ala-Phe-Gly-Tyr-NH-NH-Z.

39. The compound of claim 1, wherein said peptide is H-Tyr-ala-Phe-Gly-NH-NH-Z.

40. The compound of claim 1, wherein said peptide is H-Tyr-ala-Phe-Gly-NH-NH-CO-CH$_2$-CH$_2$-CH$_3$.

41. The compound of claim 1, wherein said peptide is H-Tyr-ala-Phe-Gly-NH-NH-tyr-H.

42. The compound of claim 1, wherein said peptide is H-Tyr-ala-Phe-Sar-NH-NH-Z.

43. The compound of claim 1, wherein said peptide is Boc-Tyr-ala-Phe-Sar-NH-NH-Z.

44. The compound of claim 1, wherein said peptide is H-Tyr-ala-Phe-Sar-Tyr-NH-NH-Z.

45. The compound of claim 1, wherein said peptide is Boc-Tyr-ala-Phe-Sar-Tyr-NH-NH-Z.

46. The compound of claim 1, wherein said peptide is H-Tyr-ala-Phe-Sar-Tyr-NH-NH-Boc.

47. The compound of claim 1, wherein said peptide is Tfa-Tyr-ala-Phe-Sar-Tyr-NH-NH-Boc.

48. The compound of claim 1, wherein said peptide is H-Tyr-ala-Phe-Gly-Tyr-NH-NH-Ph.

49. The compound of claim 1, wherein said peptide is Boc-Tyr-ala-Phe-Gly-Tyr-NH-NH-Ph.

50. The compound of claim 1, wherein said peptide is H-Tyr-ala-Phe-Gly-Tyr-NH-NH-Boc.

51. The compound of claim 1, wherein said peptide is Tfa-Tyr-ala-Phe-Gly-Tyr-NH-NH-Boc.

52. The compound of claim 1, wherein said peptide is H-Tyr-ala-Phe-Gly-Tyr-NH-NH-Adoc.

53. The compound of claim 1, wherein said peptide is Tfa-Tyr-ala-Phe-Gly-Tyr-NH-NH-Adoc.

54. The compound of claim 1, wherein said peptide is H-Tyr-ala-Phe-Gly-Tyr-NH-NH-Ad.

55. The compound of claim 1, wherein said peptide is Boc-Tyr-ala-Phe-Gly-Tyr-NH-NH-Ad.

56. The compound of claim 1, wherein said peptide is H-Tyr-ala-Phe-Gly-Leu-NH$_2$.

57. The compound of claim 1, wherein said peptide is H-Tyr-ala-Phe-Gly-Met-NH$_2$.

58. The compound of claim 1, wherein said peptide is H-Tyr-ala-Phe-Sar-Tyr-Pro-Ser-NH$_2$.
59. The compound of claim 1, wherein said peptide is H-Tyr-ala-Phe-Gly-Gly-Pro-Ser-NH$_2$.
60. The compound of claim 1, wherein said peptide is H-Tyr-ala-Phe-Gly-Tyr-Pro-Ser-NHMe.
61. The compound of claim 1, wherein said peptide is H-Tyr-ala-Phe-Gly-Tyr-Pro-Ser-NHEt.
62. The compound of claim 1, wherein said peptide is H-Tyr-ala-Phe-Gly-Tyr-Pro-Ser-OMe.
63. The compound of claim 1, wherein said peptide is H-Tyr-met-Phe-Gly-NHNHZ.
64. The compound of claim 1, wherein said peptide is H-Tyr-met(O)-Phe-Gly-NHNHZ.
65. The compound of claim 1, wherein said peptide is H-Tyr-ala-Phe-Gly-NHNHLrl.
66. The compound of claim 1, wherein said peptide is H-Tyr-ala-Phe-Gly-NHNHBnl.
67. The compound of claim 1, wherein said peptide is H-Tyr-ala-Phe-Gly-tyrNHNH$_2$.
68. The compound of claim 1, wherein said peptide is H-Tyr-ala-Phe-Gly-NHNHAdoc.
69. The compound of claim 1, wherein said peptide is H-Tyr-ala-Phe-Gly-NHNHBoc.
70. The compound of claim 1, wherein said peptide is H-Tyr-ala-Phe-Gly-Pro-NH$_2$.
71. The compound of claim 1, wherein said peptide is H-Tyr-ala-Phe-Gly-Ser-NH$_2$.
72. The compound of claim 1, wherein said peptide is H-Tyr-ala-Phe-Gly-tyr-NH$_2$.
73. The compound of claim 1, wherein said peptide is H-Tyr-ala-Phe-Sar-Tyr-NH$_2$.
74. The compound of claim 1, wherein said peptide is H-Tyr-ala-Phe-Gly-Tyr-Sar-Ser-NH$_2$.
75. The compound of claim 1, wherein said peptide is H-Tyr-ala-Phe-Gly-Pro-Ser-NH$_2$.
76. The compound of claim 1, wherein said peptide is H-Tyr-ala-Phe-Gly-Tyr-Pro-Ser-NH-NH$_2$.
77. The compound of claim 1, wherein said peptide is H-Tyr-met-Phe-Gly-Tyr-NH$_2$.
78. The compound of claim 1, wherein said peptide is H-Tyr-met-Phe-Gly-Tyr-Pro-Ser-NH$_2$.
79. The compound of claim 1, wherein said peptide is H-Tyr-ala-Phe-Pro-Tyr-Pro-Ser-NH$_2$.
80. The compound of claim 1, wherein said peptide is H-Tyr-ala-Phe-MePhe-Tyr-Pro-Ser-OMe.
81. The compound of claim 1, wherein said peptide is H-Tyr-ala-Phe-Gly-Tyr-Ppa-Ser-NH$_2$.
82. The compound of claim 1, wherein said peptide is H-Tyr-ala-Phe-Gly-Tyr-Aze-Ser-NH$_2$.
83. The compound of claim 1, wherein said peptide is H-Tyr-ala-Phe-Gly-Tyr-Tia-Ser-NH$_2$.
84. The compound of claim 1, wherein said peptide is H-Tyr-ala-Phe-Gly-Tyr-ΔPr-Ser-NH$_2$.
85. The compound of claim 1, wherein said peptide is H-Tyr-ala-Phe-Gly-Phe(NO$_2$)-Pro-Ser-NH$_2$.
86. The compound of claim 1, wherein said peptide is H-Tyr-ala-Phe-Gly-Tyr-Pro-Abu-NH$_2$.
87. The compound of claim 1, wherein said peptide is H-Tyr-ala-Phe-Gly-Tyr-Pro-Gly-NH$_2$.
88. The compound of claim 1, wherein said peptide is H-Tyr-ala-Phe-Gly-Tyr(Bzl)-Pro-Ser(Bzl)-NH$_2$.
89. The compound of claim 1, wherein said peptide is H-Tyr-ala-Phe-Gly-Tyr-Pro-Ser(Bzl)-NH$_2$.
90. The compound of claim 1, wherein said peptide is H-Tyr-ala-Phe-Gly-Tyr-NH-Ad.
91. The compound of claim 1, wherein said peptide is H-Tyr-ala-Phe-Gly-Tyr-Pro-Ser-OH.
92. The compound of claim 1, wherein said peptide is H-Tyr-ala-Phe-Gly-Tyr-NH-CH$_2$CF$_3$.
93. The compound of claim 1, wherein said peptide is H-Tyr-met-Phe-Gly-NHNH$_2$.
94. The compound of claim 1, wherein said peptide is H-Tyr-ala-Phe-Gly-tyr-NHNHZ.
95. The compound of claim 1, wherein said peptide is H-Tyr-ala-Phe-Gly-Met(O)-NH$_2$.
96. The compound of claim 1, wherein said peptide is H-Tyr-ala-Phe-Gly-Nva-NH$_2$.
97. The compound of claim 1, wherein said peptide is H-Tyr-met-Phe-Gly-Pro-NH$_2$.
98. The compound of claim 1, wherein said peptide is H-Tyr-met-Phe-Gly-Nva-NH$_2$.
99. The compound of claim 1, wherein said peptide is H-Tyr-met(O)-Phe-Gly-Tyr-Pro-Ser-NH$_2$.
100. The compound of claim 1, wherein said peptide is H-Tyr-ala-Phe-Sar-Tyr-Hyp-Ser-NH$_2$.
101. The compound of claim 1, wherein said peptide is H-Tyr-ala-Phe-Sar-Tyr(Bzl)-Hyp-Ser(Bzl)-NH$_2$.
102. The compound of claim 1, wherein said peptide is H-Tyr-ala-Phe-Gly-Tyr(Bzl)-Ppa-Ser-NH$_2$.
103. The compound of claim 1, wherein said peptide is H-Tyr-ala-Phe-Gly-Tyr-alloHyp-Ser-NH$_2$.
104. The compound of claim 1, wherein said peptide is H-Tyr-ala-Phe-Gly-Tyr-3Hyp-Ser-NH$_2$.
105. The compound of claim 1, wherein said peptide is H-Tyr-ala-Phe-Gly-Tyr(Bzl)-3Hyp-Ser(Bzl)-NH$_2$.
106. The compound of claim 1, wherein said peptide is H-Tyr-ala-Phe-Gly-Tyr(Bzl)-Aze-Ser-NH$_2$.
107. The compound of claim 1, wherein said peptide is H-Tyr-ala-Phe-Gly-Tyr(Bzl)-Tia-Ser-NH$_2$.
108. The compound of claim 1, wherein said peptide is H-Tyr-ala-Phe-Gly-Tyr(Bzl)-ΔPr-Ser-NH$_2$.
109. The compound of claim 1, wherein said peptide is H-Tyr-ala-Phe-Gly-Tyr-βAla-Ser-NH$_2$.
110. The compound of claim 1, wherein said peptide is H-Tyr-ala-Phe-Gly-Phe(F)-Pro-Ser-NH$_2$.
111. The compound of claim 1, wherein said peptide is H-Tyr-ala-Phe-Gly-Cha-Pro-Ser-NH$_2$.
112. The compound of claim 1, wherein said peptide is H-Tyr-ala-Phe-Gly-Phg-Pro-Ser-NH$_2$.
113. The compound of claim 1, wherein said peptide is H-Tyr-ala-Phe-Gly-Tyr(Me)-Pro-Ser-NH$_2$.
114. The compound of claim 1, wherein said peptide is H-Tyr-ala-Phe-Gly-Tyr-Pro-Ser-NH-CH(CH$_3$)$_2$.
115. The compound of claim 1, wherein said peptide is H-Tyr-met(O)-Phe-Gly-NHNH$_2$.
116. The compound of claim 1, wherein said peptide is H-Tyr-ala-Phe-Sar-Tyr-NHNH$_2$.
117. The compound of claim 1, wherein said peptide is H-Tyr-ala-Phe-Phe-NH-NH$_2$.
118. The compound of claim 1, wherein said peptide is H-Tyr-ala-Phe-MePhe-Tyr-Pro-Ser-NH$_2$.
119. The compound of claim 1, wherein said peptide is H-Tyr-ala-Phe-Gly-Tyr-MeAla-Ser-NH$_2$.
120. A compound defined in claim 1, wherein the peptide is H-Tyr-ala-Phe-Phe-NH-NHZ.
121. The compound of claim 1, wherein said peptide is H-Tyr-ala-Phe-Gly-Tyr-NH-NH$_2$.
122. The compound of claim 1, wherein said peptide is H-Tyr-ala-Phe-Gly-Leu-NH-NHZ.
123. The compound of claim 1, wherein said peptide is H-Tyr-ala-Phe-Gly-Tyr(Me)-Hyp-Ser-NH$_2$.
124. The compound of claim 1, wherein said peptide is H-Tyr-ala-Phe-Tyr(Bzl)-alloHyp-Ser(Bzl)-NH$_2$.
125. The compound of claim 1, wherein said peptide is H-Tyr-ala-Phe-MePhe-Tyr-Pro-Ser-OH.

126. The compound of claim 1, wherein said peptide is H-Tyr-ala-Phe-Sar-Tyr(Bzl)-Pro-Ser-NH$_2$.

127. The compound of claim 1, wherein said peptide is H-Tyr-ala-Phe-Pro-Tyr(Bzl)-Pro-Ser-NH$_2$.

128. The compound of claim 1, wherein said peptide is H-Tyr-ala-Phe-Pro-Tyr-Hyp-Ser-NH$_2$.

129. The compound of claim 1, wherein said peptide is H-Tyr-ala-Phe-Pro-Tyr(Bzl)-Hyp-Ser(Bzl)-NH$_2$.

130. The compound of claim 1, wherein said pharmacentically acceptable salt is selected from the group consisting of trifluoroacetic acid, hydrofluoric acid, hydroboric acid, acetic acid, and hydrochloric acid.

131. The compound of claim 1, wherein said peptide is H-Tyr-ala-Phe-Gly-Tyr-3alloHyp-Ser-NH$_2$.

* * * * *